US012799093B2

(12) United States Patent
García

(10) Patent No.: US 12,799,093 B2
(45) Date of Patent: Nov. 17, 2026

(54) COMPOUND, INTERMEDIATE OF THE COMPOUND, PROCESS FOR PREPARING THE COMPOUND, ORGANIC SEMICONDUCTING MATERIAL COMPRISING THE COMPOUND, ORGANIC ELECTRONIC DEVICE COMPRISING THE SAME, AND DISPLAY DEVICE AND LIGHTING DEVICE COMPRISING THE SAME

(71) Applicant: Novaled GmbH, Dresden (DE)

(72) Inventor: Elena Galàn García, Dresden (DE)

(73) Assignee: Novaled GmbH, Dresden (DE)

( * ) Notice: Subject to any disclaimer, the term of this patent is extended or adjusted under 35 U.S.C. 154(b) by 1017 days.

(21) Appl. No.: 18/000,597

(22) PCT Filed: Jun. 2, 2021

(86) PCT No.: PCT/EP2021/064813
§ 371 (c)(1),
(2) Date: Dec. 2, 2022

(87) PCT Pub. No.: WO2021/245142
PCT Pub. Date: Dec. 9, 2021

(65) Prior Publication Data

US 2023/0212141 A1 Jul. 6, 2023

(30) Foreign Application Priority Data

Jun. 3, 2020 (EP) .................................... 20177947

(51) Int. Cl.
*H01L 51/50* (2006.01)
*C07D 401/10* (2006.01)
(Continued)

(52) U.S. Cl.
CPC ......... *C07D 401/10* (2013.01); *C07D 401/14* (2013.01); *C07D 405/14* (2013.01);
(Continued)

(58) Field of Classification Search
None
See application file for complete search history.

(56) References Cited

FOREIGN PATENT DOCUMENTS

| | | |
|---|---|---|
| CN | 102482279 A | 5/2012 |
| CN | 108431980 A | 8/2018 |

(Continued)

OTHER PUBLICATIONS

Han et. at., Tetraphenylbenzene-based AIEgens: horizontally oriented emitters for highly efficient non-doped deep blue OLEDs and hosts for high-performance hybrid WOLEDs†; 2020; J. Mater. Chem. C, Aug. 2020, 7012 (Year: 2020).*

(Continued)

*Primary Examiner* — Gregory D Clark
(74) *Attorney, Agent, or Firm* — Eversheds Sutherland (US) LLP

(57) ABSTRACT

The present invention relates to a compound having the Formula (I) an intermediate of the compound, a process for preparing the compound, an organic semiconducting material comprising the compound and an organic electronic
(Continued)

device comprising the same. The invention further relates to a display device or a lighting device comprising the organic electronic device.

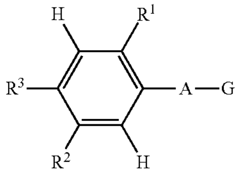

(I)

15 Claims, 2 Drawing Sheets

(51) Int. Cl.

| | |
|---|---|
| ***C07D 401/14*** | (2006.01) |
| ***C07D 405/14*** | (2006.01) |
| ***H10K 50/16*** | (2023.01) |
| ***H10K 50/17*** | (2023.01) |
| ***H10K 50/18*** | (2023.01) |
| ***H10K 85/60*** | (2023.01) |

(52) U.S. Cl.
CPC .......... *H10K 50/16* (2023.02); *H10K 50/171* (2023.02); *H10K 50/18* (2023.02); *H10K 85/652* (2023.02); *H10K 85/654* (2023.02); *H10K 85/6574* (2023.02)

(56) References Cited

FOREIGN PATENT DOCUMENTS

| | | | | | |
|---|---|---|---|---|---|
| CN | 110105244 | A | * | 8/2019 | ............ H01L 51/54 |
| EP | 3312895 | A1 | | 10/2016 | |
| EP | 3312896 | A1 | | 10/2016 | |
| EP | 3312899 | A1 | | 10/2016 | |
| EP | 3502106 | A1 | | 12/2017 | |
| EP | 3653619 | A1 | | 5/2020 | |
| EP | 3925958 | A1 | | 12/2021 | |
| JP | 2007169187 | A | | 7/2007 | |
| JP | 2014103103 | A | | 6/2014 | |
| WO | 2018077689 | A1 | | 5/2018 | |
| WO | 2019121672 | A1 | | 6/2019 | |

OTHER PUBLICATIONS

Communication pursuant to Article 94(3) EPC issued in European application No. 20177947.7, dated Nov. 24, 2023 (8 pages).

International Search Report and Written Opinion issued in international application No. PCT/EP2021/064813, mailed Sep. 10, 2021, 16 pages.

Han, Pengbo et al., Tetraphenylbenzene-based AIEgens: horizontally oriented emitters for highly efficient non-doped deep blue OLEDs and hosts for high-performance hybrid WOLEDs, Journal of Materials Chemistry C, vol. 8, No. 21, Apr. 7, 2020, pp. 7012-7018.

Office Action issued in Taiwan application No. 110120131, dated Jul. 28, 2025 (11 pages).

Notification of First Office Action issued in China application No. 202180039880.1, dated Jul. 10, 2025 (14 pages).

* cited by examiner

COMPOUND, INTERMEDIATE OF THE COMPOUND, PROCESS FOR PREPARING THE COMPOUND, ORGANIC SEMICONDUCTING MATERIAL COMPRISING THE COMPOUND, ORGANIC ELECTRONIC DEVICE COMPRISING THE SAME, AND DISPLAY DEVICE AND LIGHTING DEVICE COMPRISING THE SAME

TECHNICAL FIELD

The present invention relates to a compound, an intermediate of the compound, a process for preparing the compound, an organic semiconducting material comprising the compound and an organic electronic device comprising the same. The invention further relates to a display device or a lighting device comprising the organic electronic device.

BACKGROUND ART

Organic light-emitting diodes (OLEDs), which are self-emitting devices, have a wide viewing angle, excellent contrast, quick response, high brightness, excellent driving voltage characteristics, and color reproduction. A typical OLED includes an anode, a hole transport layer (HTL), an emission layer (EML), an electron transport layer (ETL), and a cathode, which are sequentially stacked on a substrate. In this regard, the HTL, the EML, and the ETL are thin films formed essentially by organic and/or organometallic compounds.

When a voltage is applied to the anode and the cathode, holes injected from the anode electrode move to the EML, via the HTL, and electrons injected from the cathode electrode move to the EML, via the ETL. The holes and electrons mainly recombine in the EML to generate excitons. When the excitons drop from an excited state to a ground state, light is emitted. The injection and flow of holes and electrons should be balanced, so that an OLED having the above-described structure has excellent efficiency.

Important role among OLED devices used in state-of-art displays play devices comprising electron transport layers doped with metal salts or metal complexes, such as e.g. lithium 8-hydroxyquinolinolate (LiQ), to improve the performance of the device.

A variety of organic compounds comprising multiple arene and/or heteroarene rings as well as the use thereof in organic electronic devices, such as OLEDs, is well known in the art, for example from WO 2018/077689 A1, EP 3 312 899 A1 EP 3 312 895 A1, EP 3 312 896 A1, and WO 2019/121672 A1.

There is, however, still an unmet demand for improved materials, specifically for electron transport matrix compounds, enabling improved voltage stability and/or lifetime in OLEDs and, more specifically, in blue light emitting OLEDs.

It is, therefore, the object of the present invention to provide organic semiconducting materials and compounds suitable for use in such materials overcoming drawbacks of the prior art, in particular to improve the voltage stability and lifetime of organic electronic devices such as (blue) OLEDs.

DISCLOSURE

The object is achieved by a compound of the following Formula (I)

(I)

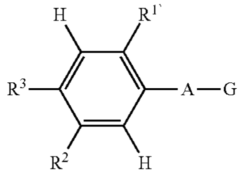

wherein

A is substituted or unsubstituted phenylene, wherein, in case that A is substituted, the one or more substituent(s) are independently selected hydrocarbyl groups;

G is (i) substituted or unsubstituted $C_{10}$ to $C_{60}$ aryl comprising at least two condensed aromatic rings; or (ii) substituted or unsubstituted $C_3$ to $C_{60}$ heteroaryl comprising at least one six-membered ring, wherein the six-membered ring comprises at least two N-atoms; or (iii) substituted or unsubstituted heteroaryl comprising at least two condensed aromatic rings, wherein at least one of the aromatic rings is an azine ring; or (iv) selected from benzofurane, benzothiophene, dibenzothiophene, naphtofurane, naphtothiophene, naphtobenzofurane, naphtobenzothiophene, dinaphtofurane, dinaphtothiophene, xanthene, thioxanthene, dibenzodioxine, phenoxazine, phenothiazine, benzimidazole, benzoxazole, and benzothiazole, wherein the respective group may be unsubstituted or substituted; or (v) selected from fluorene, benzofluorene, dibenzofluorene, naphtofluorene, dinaphtofluorene, benzonaphtofluorene, 9-silafluorene, benzo 9-silafluorene, dibenzo 9-silafluorene, naphto 9-silafluorene, dinaphto 9-silafluorene, and benzonaphto 9-silafluorene;

$R^1$ is (i) H; or (ii) substituted or unsubstituted pyridyl, wherein, in case that $R^1$ is substituted, the one or more substituent(s) are independently selected from the group consisting of $C_1$ to $C_{20}$ aliphatic hydrocarbyl and nitrile; or (iii) substituted or unsubstituted phenyl, wherein, in case that $R^1$ is substituted, the one or more substituent(s) are nitrile; or (iv) a phosphine oxide group;

$R^2$ and $R^3$ are independently (i) substituted or unsubstituted pyridyl, wherein, in case that $R^2$ and/or $R^3$ are substituted, the one or more substituent(s) are independently selected from the group consisting of $C_1$ to $C_{20}$ aliphatic hydrocarbyl and nitrile; or (ii) substituted or unsubstituted phenyl wherein, in case that $R^2$ and/or $R^3$ are substituted, the one or more substituent(s) are independently selected from the group consisting of $C_1$ to $C_{20}$ aliphatic hydrocarbyl and nitrile; or (iii) a phosphine oxide group;

with the proviso that at least one of $R^1$, $R^2$ and $R^3$ is (i) substituted or unsubstituted pyridyl, wherein the one or more substituent(s) on the pyridyl, if present, are independently selected from the group consisting of $C_1$ to $C_{20}$ aliphatic hydrocarbyl and nitrile; or
(ii) substituted phenyl wherein
(a) the one or more substituent(s) of the phenyl are independently selected from the group consisting of $C_1$ to $C_{20}$ aliphatic hydrocarbyl and nitrile, and
(b) at least one of the substituents is nitrile; or
(iii) a phosphine oxide group.

In the compound of Formula (I), A may be substituted or unsubstituted phenylene, wherein, in case that A is substituted, the one or more substituent(s) are independently selected aliphatic hydrocarbon groups. A may be substituted or unsubstituted phenylene, wherein, in case that A is substituted, the one or more substituent(s) are independently selected from the group consisting of $C_1$ to $C_{20}$ alkyl or $C_3$ to $C_{20}$ cycloalkyl, alternatively $C_1$ to $C_{12}$ alkyl or $C_3$ to $C_{12}$ cycloalkyl, alternatively $C_1$ to $C_4$ alkyl or $C_5$ to $C_6$ cycloalkyl. In case that A is substituted, it may be provided that the substituents are not linked with each other to form a ring.

A may be unsubstituted phenylene. A may be selected from unsubstituted o-phenylene, unsubstituted m-phenylene and unsubstituted p-phenylene. A may be unsubstituted p-phenylene.

G may be
(i) substituted or unsubstituted $C_{10}$ to $C_{54}$ aryl, alternatively $C_{10}$ to $C_{48}$ aryl, alternatively $C_{10}$ to $C_{42}$ aryl, alternatively $C_{10}$ to $C_{36}$ aryl, alternatively $C_{10}$ to $C_{30}$ aryl, comprising at least two condensed aromatic rings; or
(ii) substituted or unsubstituted $C_3$ to $C_{60}$ heteroaryl, alternatively $C_3$ to $C_{54}$ heteroaryl, alternatively $C_3$ to $C_{48}$ heteroaryl, alternatively $C_3$ to $C_{42}$ alternatively $C_3$ to $C_{36}$ heteroaryl, $C_3$ to $C_{30}$ heteroaryl, comprising at least one six-membered ring, wherein the six-membered ring comprises at least two N-atoms; or
(iii) substituted or unsubstituted $C_3$ to $C_{60}$ heteroaryl, alternatively $C_3$ to $C_{54}$ heteroaryl, alternatively $C_3$ to $C_{48}$ heteroaryl, alternatively $C_3$ to $C_{42}$ alternatively $C_3$ to $C_{36}$ heteroaryl, $C_3$ to $C_{30}$ heteroaryl, comprising at least two condensed aromatic rings, wherein at least one of the aromatic rings is an azine ring; or
(iv) selected from benzofurane, benzothiophene, dibenzothiophene, naphtofurane, naphtothiophene, naphtobenzofurane, naphtobenzothiophene, dinaphtofurane, dinaphtothiophene, xanthene, thioxanthene, dibenzodioxine, phenoxazine, phenothiazine, benzimidazole, benzoxazole, and benzothiazole, wherein the respective group may be unsubstituted or substituted; or
(v) selected from fluorene, benzofluorene, dibenzofluorene, naphtofluorene, dinaphtofluorene, benzonaphtofluorene.

In another embodiment, G may be
(i) substituted or unsubstituted $C_{10}$ to $C_{60}$ aryl, alternatively $C_{10}$ to $C_{54}$ aryl, alternatively $C_{10}$ to $C_{48}$ aryl, alternatively $C_{10}$ to $C_{42}$ aryl, alternatively $C_{10}$ to $C_{36}$ aryl, alternatively $C_{10}$ to $C_{30}$ aryl, comprising at least two condensed aromatic rings; or
(ii) substituted or unsubstituted $C_3$ to $C_{60}$ heteroaryl, alternatively $C_{10}$ to $C_{54}$ aryl, alternatively $C_{10}$ to $C_{48}$ aryl, alternatively $C_{10}$ to $C_{42}$ aryl, alternatively $C_{10}$ to $C_{36}$ aryl, alternatively $C_{10}$ to $C_{30}$ aryl, comprising at least one six-membered ring, wherein the six-membered ring comprises at least two N-atoms; or
(iii) substituted or unsubstituted heteroaryl, alternatively $C_3$ to $C_{60}$ heteroaryl, alternatively $C_3$ to $C_{54}$ heteroaryl, alternatively $C_3$ to $C_{48}$ heteroaryl, alternatively $C_3$ to $C_{42}$ alternatively $C_3$ to $C_{36}$ heteroaryl, $C_3$ to $C_{30}$ heteroaryl, comprising at least two condensed aromatic rings, wherein at least one of the aromatic rings is an azine ring.

In case that G is substituted, the one or more substituents included in G may be independently selected from the group consisting of deuterium, halogen, CN, $C_1$-$C_{20}$ linear alkyl, $C_3$-$C_{20}$ branched alkyl, $C_3$-$C_{20}$ cyclic alkyl, $C_1$-$C_{20}$ linear alkoxy, $C_3$-$C_{20}$ branched alkoxy, $C_1$-$C_{12}$ linear fluorinated alkyl, $C_1$-$C_{12}$ linear fluorinated alkoxy, $C_3$-$C_{12}$ branched fluorinated cyclic alkyl, $C_3$-$C_{12}$ fluorinated cyclic alkyl, $C_3$-$C_{12}$ fluorinated cyclic alkoxy, RCN, $C_6$-$C_{60}$ aryl, $C_2$-$C_{60}$ heteroaryl, OR, SR, (C═O)R, (C═O)$NR_2$, $SiR_3$, (S═O)R, $(S{=}O)_2R$, $(P{=}O)R_2$; wherein each R independently selected from $C_1$-$C_{20}$ linear alkyl, $C_1$-$C_{20}$ alkoxy, $C_1$-$C_{20}$ thioalkyl, $C_3$-$C_{20}$ branched alkyl, $C_3$-$C_{20}$ cyclic alkyl, $C_3$-$C_{20}$ branched alkoxy, $C_3$-$C_{20}$ cyclic alkoxy, $C_3$-$C_{20}$ branched thioalkyl, $C_3$-$C_{20}$ cyclic thioalkyl, $C_6$-$C_{20}$ aryl and $C_2$-$C_{20}$ heteroaryl.

G may be selected from anthracene, phenanthrene, pyrene, tetracene, pentacene, chrysene, fluoranthene, benzofluoranthene, triphenylene, quinoline, isoquinoline, benzoquinoline, cinnoline, phtalazine, quinazoline, quinoxaline, naphtyridine, pyrazine, triazine, phenanthridine, phenanthroline, acridine, benzoacridine and dibenzoacridine; wherein the respective group may be substituted or unsubstituted.

G may be substituted or unsubstituted $C_3$ to $C_{60}$ heteroaryl comprising at least one six-membered ring, wherein the six-membered ring comprises at least two N-atoms. G is substituted $C_3$ to $C_{60}$ heteroaryl comprising at least one six-membered ring, wherein the six-membered ring comprises at least two N-atoms.

G may be represented by the following Formula (II)

(II)

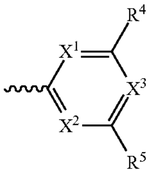

wherein
 represents the binding to the group A;
$X^1$ to $X^3$ are independently selected from the group consisting of N and CH, wherein at least two of $X^1$ to $X^3$ are N; and
$R^4$ and $R^5$ are independently selected from the group consisting of substituted or unsubstituted $C_6$ to $C_{30}$ aryl and substituted or unsubstituted $C_3$ to $C_{30}$ heteroaryl.

In case that $R^4$ and/or $R^5$ is substituted, the one or more substituents included in $R^4$ and/or $R^5$ may be independently selected from the group consisting of deuterium, halogen, CN, $C_1$-$C_{20}$ linear alkyl, $C_3$-$C_{20}$ branched alkyl, $C_3$-$C_{20}$ cyclic alkyl, $C_1$-$C_{20}$ linear alkoxy, $C_3$-$C_{20}$ branched alkoxy, $C_1$-$C_{12}$ linear fluorinated alkyl, $C_1$-$C_{12}$ linear fluorinated alkoxy, $C_3$-$C_{12}$ branched fluorinated cyclic alkyl, $C_3$-$C_{12}$ fluorinated cyclic alkyl, $C_3$-$C_{12}$ fluorinated cyclic alkoxy, RCN, $C_6$-$C_{60}$ aryl, $C_2$-$C_{60}$ heteroaryl, OR, SR, (C═O)R, (C═O)$NR_2$, $SiR_3$, (S═O)R, $(S{=}O)_2R$, $(P{=}O)R_2$; wherein each R independently selected from $C_1$-$C_{20}$ linear alkyl, $C_1$-$C_{20}$ alkoxy, $C_1$-$C_{20}$ thioalkyl, $C_3$-$C_{20}$ branched alkyl, $C_3$-$C_{20}$ cyclic alkyl, $C_3$-$C_{20}$ branched alkoxy, $C_3$-$C_{20}$ cyclic alkoxy, $C_3$-$C_{20}$ branched thioalkyl, $C_3$-$C_{20}$ cyclic thioalkyl, $C_6$-$C_{20}$ aryl and $C_2$-$C_{20}$ heteroaryl.

G may be represented by the following Formula (III)

(III)

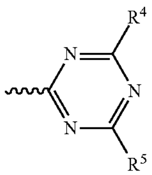

wherein

 represents the binding to the group A; and $R^4$ and $R^5$ are independently selected from the group consisting of $C_6$ to $C_{30}$ aryl and $C_3$ to $C_{30}$ heteroaryl.

In Formula (II) and Formula (III), $R^4$ and $R^5$ may be independently selected from the group consisting of $C_6$ to $C_{18}$ aryl and $C_3$ to $C_{18}$ heteroaryl. In Formula (II) and Formula (III) $R^4$ and $R^5$ may be independently selected from the group consisting of $C_6$ to $C_{12}$ aryl and $C_3$ to $C_{12}$ heteroaryl. In Formula (II) and Formula (III) $R^4$ and $R^5$ may be independently selected from the group consisting of phenyl, anthracenyl, biphenyl, and dibenzofuranyl. In Formula (II) and Formula (III) $R^4$ and $R^5$ may be independently selected from the group consisting of phenyl, anthracenyl, and dibenzofuranyl.

G may be a group having one of the following formulas G-1 to G-8 wherein "" represents the binding to the group A

G-1

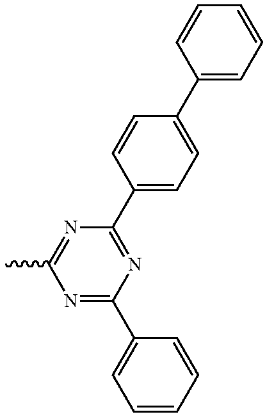

,

G-2

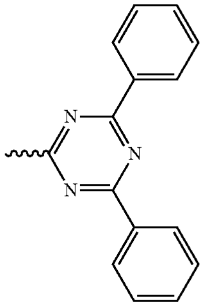

,

-continued

G-3

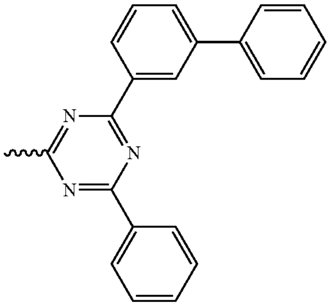

,

G-4

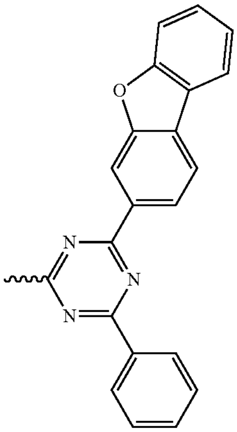

,

G-5

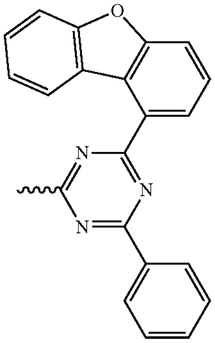

,

G-6

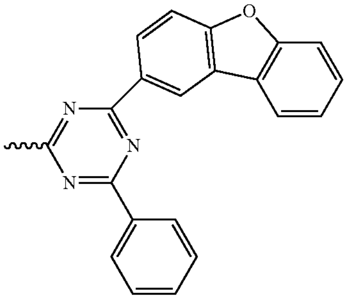

,

-continued

G-7

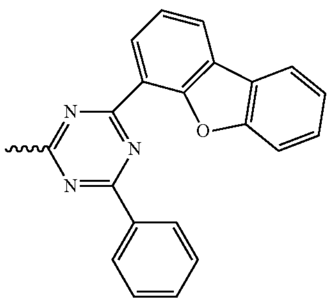

,

G-8

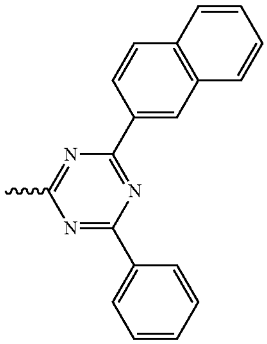

,

G-9

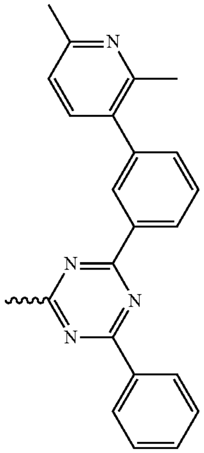

.

In particular, G may be selected from the above groups G-2, G-4, G-8 and G-9.

$R^1$ may be (i) H; or (ii) substituted or unsubstituted pyridyl, wherein, in case that $R^1$ is substituted, the one or more substituent(s) are independently selected from the group consisting of $C_1$ to $C_{12}$, alternatively $C_1$ to $C_6$, alternatively $C_1$ to $C_4$ aliphatic hydrocarbyl and nitrile; or (iii) substituted or unsubstituted phenyl, wherein, in case that $R^1$ is substituted, the one or more substituent(s) are nitrile.

$R^1$ may be (i) H; or (ii) substituted or unsubstituted pyridyl, wherein, in case that $R^1$ is substituted, the one or more substituent(s) are independently selected from the group consisting of $C_1$ to $C_6$, alternatively $C_1$ to $C_4$ alkyl; or (iii) substituted or unsubstituted phenyl, wherein, in case that $R^1$ is substituted, the one or more substituent(s) are nitrile.

$R^1$ may be H, phenyl, pyridyl or phenyl substituted with one nitrile. $R^1$ may be H or phenyl. $R^1$ may be phenyl.

$R^2$ and $R^3$ may be independently (i) substituted or unsubstituted pyridyl, wherein, in case that $R^2$ and/or $R^3$ are substituted, the one or more substituent(s) are independently selected from the group consisting of $C_1$ to $C_{12}$, alternatively $C_1$ to $C_6$, alternatively $C_1$ to $C_4$ aliphatic hydrocarbyl and nitrile; or (ii) substituted or unsubstituted phenyl wherein, in case that $R^2$ and/or $R^3$ are substituted, the one or more substituent(s) are independently selected from the group consisting of $C_1$ to $C_{12}$, alternatively $C_1$ to $C_6$, alternatively $C_1$ to $C_4$ aliphatic hydrocarbyl and nitrile; or (iii) a phosphine oxide group.

$R^2$ and $R^3$ may be independently (i) substituted or unsubstituted pyridyl, wherein, in case that $R^2$ and/or $R^3$ are substituted, the one or more substituent(s) are independently selected from the group consisting of $C_1$ to $C_6$, alternatively $C_1$ to $C_4$ alkyl; or (ii) substituted or unsubstituted phenyl wherein, in case that $R^2$ and/or $R^3$ are substituted, the one or more substituent(s) are independently selected from the group consisting of $C_1$ to $C_6$, alternatively $C_1$ to $C_4$ alkyl and nitrile.

$R^2$ and $R^3$ may be independently selected from the group consisting of phenyl, pyridyl and phenyl substituted with one nitrile.

$R^2$ may be selected from pyridine-2-yl, pyridine-3-yl and pyridine-4-yl. $R^3$ may be selected from pyridine-2-yl, pyridine-3-yl and pyridine-4-yl.

$R^1$ and $R^2$ may be pyridyl or phenyl substituted with at least one nitrile group.

$R^1$, $R^2$ and $R^3$ may be unsubstituted phenyl or phenyl substituted with at least one $C_1$ to $C_{20}$ aliphatic hydrocarbyl.

$R^2$ and $R^3$ may be selected from unsubstituted pyridyl, pyridyl substituted with at least one $C_1$ to $C_{20}$ aliphatic hydrocarbyl, and phenyl substituted with at least one nitrile group.

$R^1$ may be phenyl and at least one of $R^2$ and $R^3$ may be selected from unsubstituted pyridyl, pyridyl substituted with at least one $C_1$ to $C_{20}$ aliphatic hydrocarbyl, and phenyl substituted with at least one nitrile group.

$R^1$ may be phenyl and $R^2$ and $R^3$ may be selected from unsubstituted pyridyl, pyridyl substituted with at least one $C_1$ to $C_{20}$ aliphatic hydrocarbyl, and phenyl substituted with at least one nitrile group.

$R^1$ may be H and at least one of $R^2$ and $R^3$ may be selected from unsubstituted pyridyl, pyridyl substituted with at least one $C_1$ to $C_{20}$ aliphatic hydrocarbyl, and phenyl substituted with at least one nitrile group.

$R^1$ may be H and $R^2$ and $R^3$ may be selected from unsubstituted pyridyl, pyridyl substituted with at least one $C_1$ to $C_{20}$ aliphatic hydrocarbyl, and phenyl substituted with at least one nitrile group.

The moiety

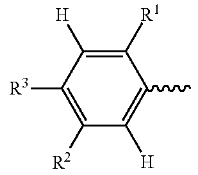

in the compound of Formula (I) (wherein  represents the binding to A) may be selected from the following groups R-1 to R-8

R-1

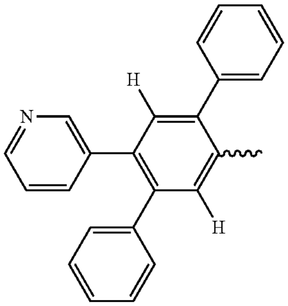

,

R-2

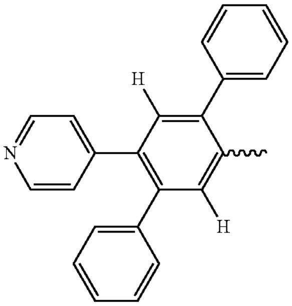

,

R-3

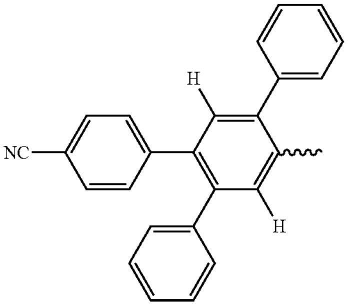

,

R-4

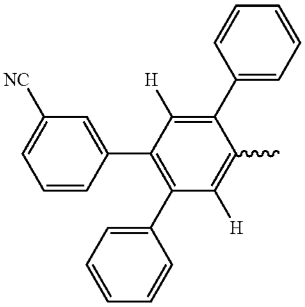

,

R-5

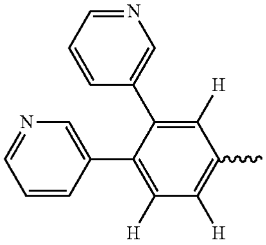

,

-continued

R-6

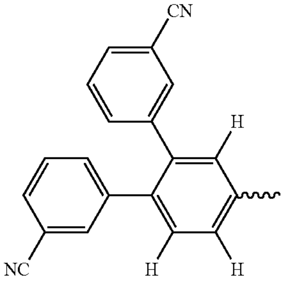

,

R-7

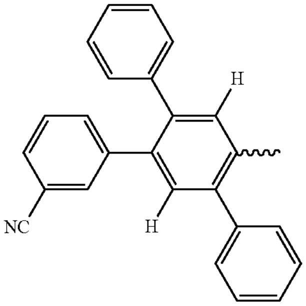

,

R-8

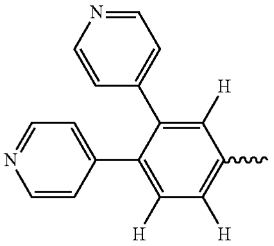

.

In particular, the moiety

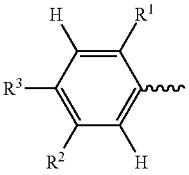

in Formula (I) may be selected from the above groups R-1 and R-2.

In Formula (I), the one or more of the phosphine oxide group(s), if present, may be dialkyl phosphine oxide. In Formula (I), the one or more of the phosphine oxide group (s), if present, may be dimethyl phosphine oxide.

In one embodiment, there is provided a compound of the following Formula (I)

(I)

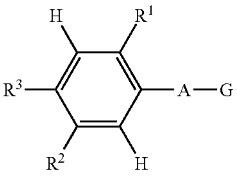

wherein

A is substituted or unsubstituted phenylene, wherein, in case that A is substituted, the one or more substituent(s) are independently selected aliphatic hydrocarbon groups;

G is (i) substituted or unsubstituted $C_{10}$ to $C_{54}$ aryl comprising at least two condensed aromatic rings; or (ii) substituted or unsubstituted $C_3$ to $C_{60}$ heteroaryl comprising at least one six-membered ring, wherein the six-membered ring comprises at least two N-atoms; or (iii) substituted or unsubstituted $C_3$ to $C_{60}$ heteroaryl comprising at least two condensed aromatic rings, wherein at least one of the aromatic rings is an azine ring; or (iv) selected from benzofurane, benzothiophene, dibenzothiophene, naphtofurane, naphtothiophene, naphtobenzofurane, naphtobenzothiophene, dinaphtofurane, dinaphtothiophene, xanthene, thioxanthene, dibenzodioxine, phenoxazine, phenothiazine, benzimidazole, benzoxazole, and benzothiazole, wherein the respective group may be unsubstituted or substituted; or (v) selected from fluorene, benzofluorene, dibenzofluorene, naphtofluorene, dinaphtofluorene, benzonaphtofluorene;

wherein in case that G is substituted, the one or more substituents included in G may be independently selected from the group consisting of deuterium, halogen, CN, $C_1$-$C_{20}$ linear alkyl, $C_3$-$C_{20}$ branched alkyl, $C_3$-$C_{20}$ cyclic alkyl, $C_1$-$C_{20}$ linear alkoxy, $C_3$-$C_{20}$ branched alkoxy, $C_1$-$C_{12}$ linear fluorinated alkyl, $C_1$-$C_{12}$ linear fluorinated alkoxy, $C_3$-$C_{12}$ branched fluorinated cyclic alkyl, $C_3$-$C_{12}$ fluorinated cyclic alkyl, $C_3$-$C_{12}$ fluorinated cyclic alkoxy, RCN, $C_6$-$C_{60}$ aryl, $C_2$-$C_{60}$ heteroaryl, OR, SR, (C═O)R, (C═O)$NR_2$, $SiR_3$, (S═O)R, ($SO_2$)R, (P═O)$R_2$; wherein each R independently selected from $C_1$-$C_{20}$ linear alkyl, $C_1$-$C_{20}$ alkoxy, $C_1$-$C_{20}$ thioalkyl, $C_3$-$C_{20}$ branched alkyl, $C_3$-$C_{20}$ cyclic alkyl, $C_3$-$C_{20}$ branched alkoxy, $C_3$-$C_{20}$ cyclic alkoxy, $C_3$-$C_{20}$ branched thioalkyl, $C_3$-$C_{20}$ cyclic thioalkyl, $C_6$-$C_{20}$ aryl and $C_2$-$C_{20}$ heteroaryl;

$R^1$ is (i) H; or (ii) substituted or unsubstituted pyridyl, wherein, in case that $R^1$ is substituted, the one or more substituent(s) are independently selected from the group consisting of $C_1$ to $C_{12}$ and nitrile; or (iii) substituted or unsubstituted phenyl, wherein, in case that $R^1$ is substituted, the one or more substituent(s) are nitrile;

$R^2$ and $R^3$ are independently (i) substituted or unsubstituted pyridyl, wherein, in case that $R^2$ and/or $R^3$ are substituted, the one or more substituent(s) are independently selected from the group consisting of $C_1$ to $C_{12}$ aliphatic hydrocarbyl and nitrile; or (ii) substituted or unsubstituted phenyl wherein, in case that $R^2$ and/or $R^3$ are substituted, the one or more substituent(s) are independently selected from the group consisting of $C_1$ to $C_{12}$ aliphatic hydrocarbyl and nitrile; or (iii) a phosphine oxide group;

with the proviso that at least one of $R^1$, $R^2$ and $R^3$ is (i) substituted or unsubstituted pyridyl, wherein the one or more substituent(s) on the pyridyl, if present, are independently selected from the group consisting of $C_1$ to $C_{12}$ aliphatic hydrocarbyl and nitrile; or (ii) substituted phenyl, wherein (a) the one or more substituent(s) of the phenyl are independently selected from the group consisting of $C_1$ to $C_{12}$ aliphatic hydrocarbyl and nitrile, and (b) at least one of the substituents is nitrile; or (iii) a phosphine oxide group.

In a further embodiment, there is provided a compound of the following Formula (I)

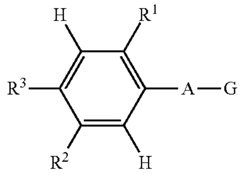

(I)

wherein

A is substituted or unsubstituted phenylene, wherein, in case that A is substituted, the one or more substituent(s) are independently selected from the group consisting of $C_1$ to $C_4$ alkyl and $C_5$ to $C_6$ cycloalkyl;

G is (i) substituted or unsubstituted $C_{10}$ to $C_{60}$ aryl comprising at least two condensed aromatic rings; or (ii) substituted or unsubstituted $C_3$ to $C_{60}$ heteroaryl comprising at least one six-membered ring, wherein the six-membered ring comprises at least two N-atoms; or (iii) substituted or unsubstituted heteroaryl, alternatively $C_3$ to $C_{60}$ heteroaryl comprising at least two condensed aromatic rings, wherein at least one of the aromatic rings is an azine ring;

$R^1$ is (i) H; or (ii) substituted or unsubstituted pyridyl, wherein, in case that $R^1$ is substituted, the one or more substituent(s) are independently selected from the group consisting of $C_1$ to $C_6$, alkyl; or (iii) substituted or unsubstituted phenyl, wherein, in case that $R^1$ is substituted, the one or more substituent(s) are nitrile;

$R^2$ and $R^3$ are independently (i) substituted or unsubstituted pyridyl, wherein, in case that $R^2$ and/or $R^3$ are substituted, the one or more substituent(s) are independently selected from the group consisting of $C_1$ to $C_6$ alkyl; or (ii) substituted or unsubstituted phenyl wherein, in case that $R^2$ and/or $R^3$ are substituted, the one or more substituent(s) are independently selected from the group consisting of $C_1$ to $C_6$ alkyl and nitrile;

with the proviso that at least one of $R^1$, $R^2$ and $R^3$ is (i) substituted or unsubstituted pyridyl, wherein the one or more substituent(s) on the pyridyl, if present, are independently selected from the group consisting of $C_1$ to $C_6$ alkyl and nitrile; or (ii) substituted phenyl wherein (a) the one or more substituent(s) of the phenyl are independently selected from the group consisting of $C_1$ to $C_6$ alkyl and nitrile, and (b) at least one of the substituents is nitrile.

In a further embodiment, there is provided a compound of the following Formula (I)

(I)

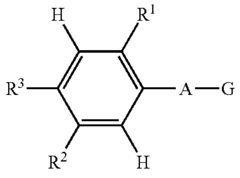

wherein

A is unsubstituted phenylene;

G is selected from anthracene, phenanthrene, pyrene, tetracene, pentacene, chrysene, fluoranthene, benzofluoranthene, triphenylene, quinoline, isoquinoline, benzoquinoline, cinnoline, phtalazine, quinazoline, quinoxaline, naphtyridine, pyrazine, triazine, phenanthridine, phenanthroline, acridine, benzoacridine and dibenzoacridine; wherein the respective group may be substituted or unsubstituted;

$R^1$ is phenyl, pyridyl or phenyl substituted with one nitrile;

$R^2$ and $R^3$ are independently selected from the group consisting of phenyl, pyridyl and phenyl substituted with one nitrile.

with the proviso that at least one of $R^1$, $R^2$ and $R^3$ is pyridyl or phenyl substituted with one nitrile.

In a further embodiment, there is provided a compound of the following Formula (I)

(I)

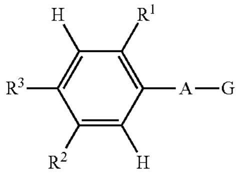

wherein

A is unsubstituted phenylene;

G is represented by the following Formula (II)

(II)

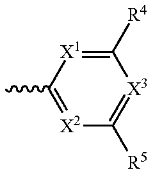

wherein represents the binding to the group A;

$X^1$ to $X^3$ are independently selected from the group consisting of N and CH, wherein at least two of $X^1$ to $X^3$ are N; and $R^4$ and $R^5$ are independently selected from the group consisting of $C_6$ to $C_{30}$ aryl and $C_3$ to $C_{30}$ heteroaryl;

$R^1$ is H or phenyl;

$R^2$ and $R^3$ are independently phenyl, pyridyl or phenyl substituted with at least one nitrile group;

with the proviso that at least one of $R^2$ and $R^3$ is pyridyl or phenyl substituted with one nitrile.

In a further embodiment, there is provided a compound of the following Formula (I)

(I)

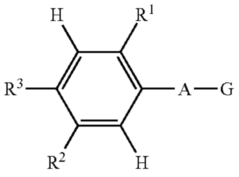

wherein

A is unsubstituted phenylene;

G is represented by the following Formula (III)

(III)

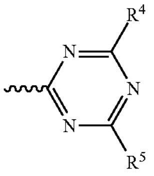

wherein represents the binding to the group A; and $R^4$ and $R^5$ are independently selected from the group consisting of $C_6$ to $C_{30}$ aryl and $C_3$ to $C_{30}$ heteroaryl;

$R^1$ is H or phenyl;

$R^2$ and $R^3$ are independently phenyl, pyridyl or phenyl substituted with at least one nitrile group;

with the proviso that at least one of $R^2$ and $R^3$ is pyridyl or phenyl substituted with one nitrile.

In a further embodiment, there is provided a compound of the following Formula (I)

(I)

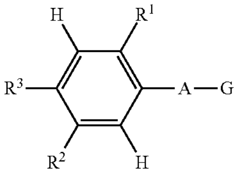

wherein

A is unsubstituted phenylene;

G is represented by one of the above Formulas G-1 to G-8; and the moiety

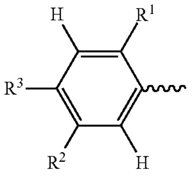

in Formula (I) (wherein  represents the binding to A) is selected from the above groups R-1 to R-8.

In a further embodiment, the compound of Formula (I) is one of the following compounds 1 to 29

-continued
1
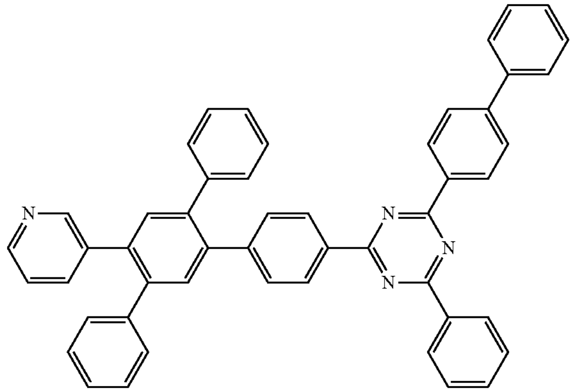
2
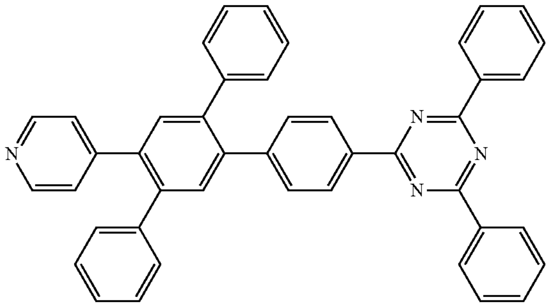
3
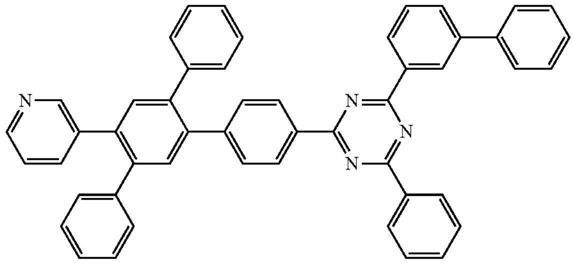
4
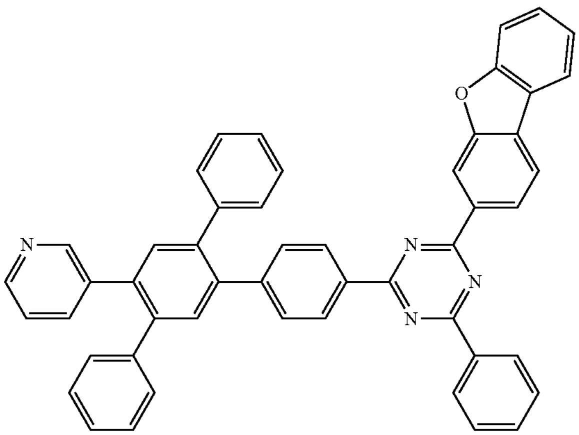
5
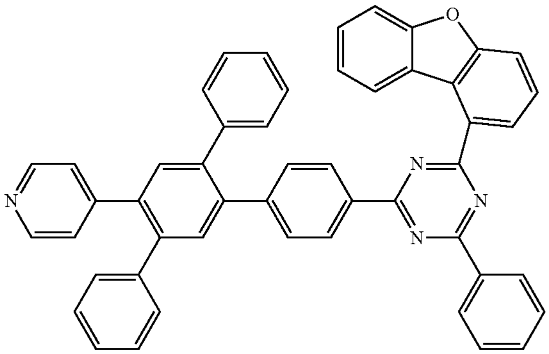
6
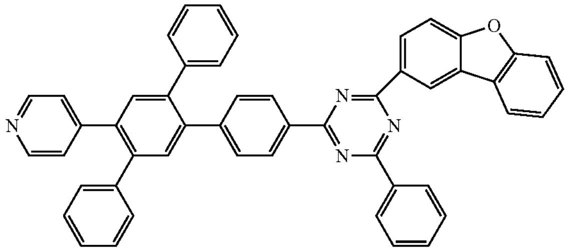
7
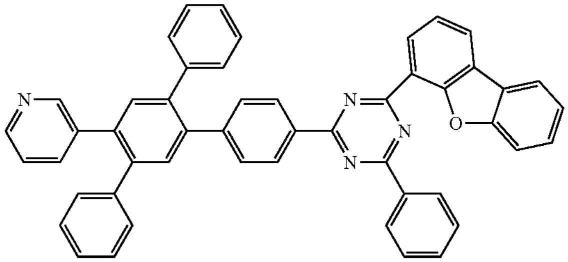
8
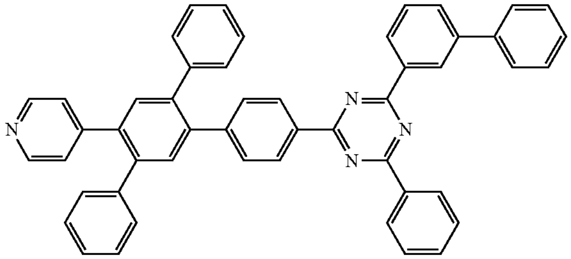
9
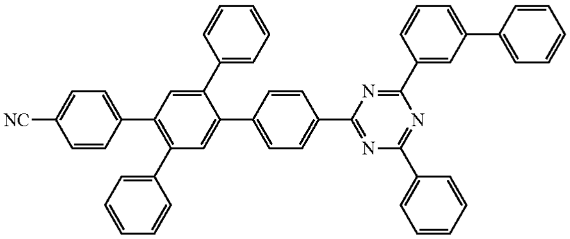

-continued
10
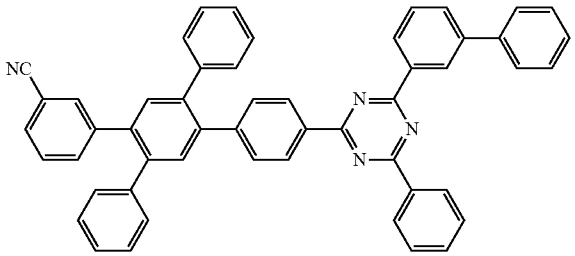
11
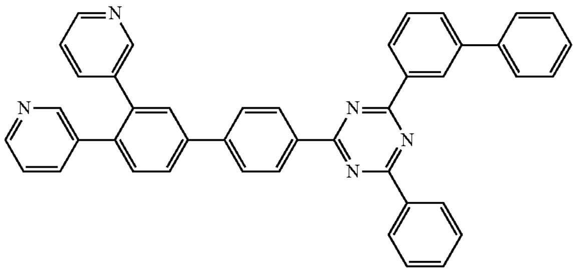
12
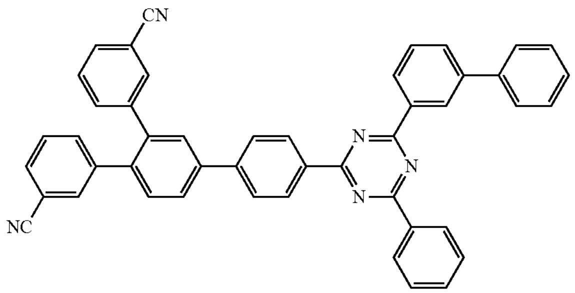
13
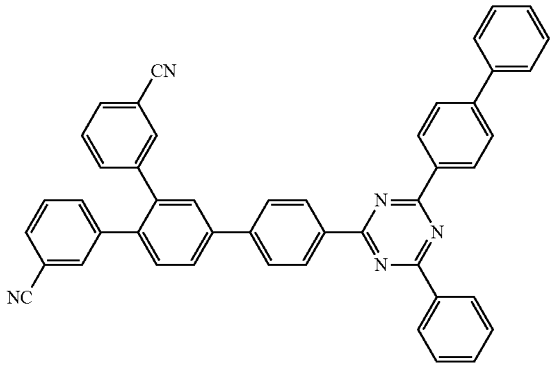
-continued
14
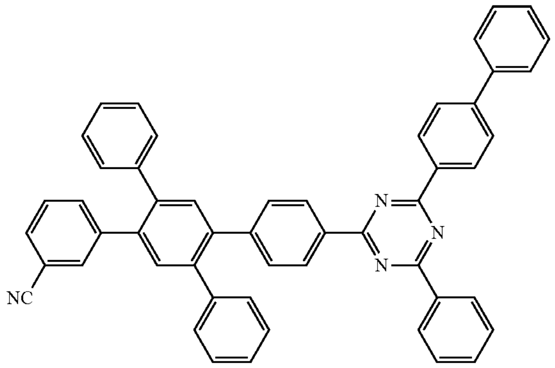
15
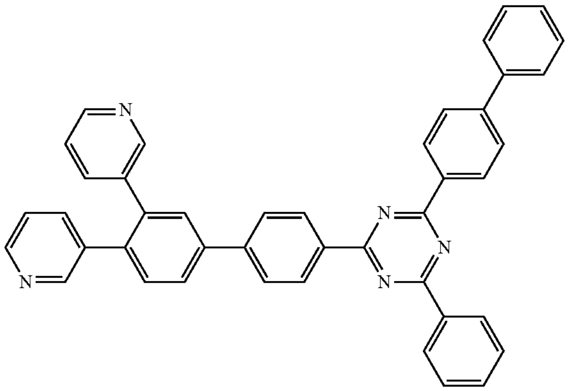
16
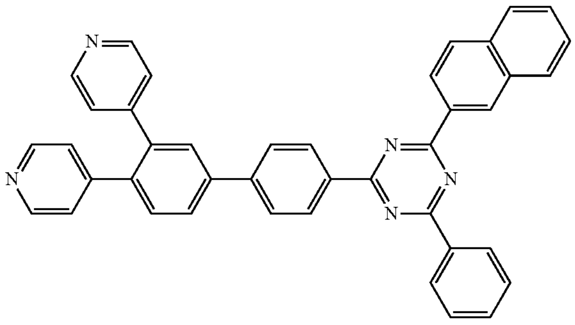
17
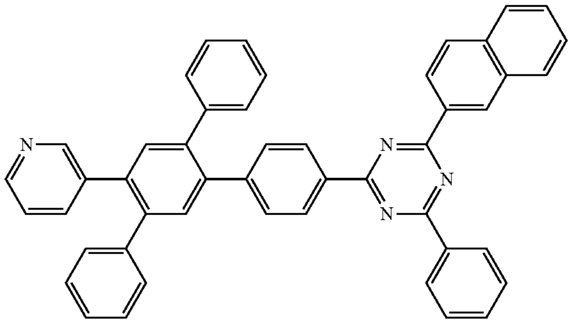

-continued
18
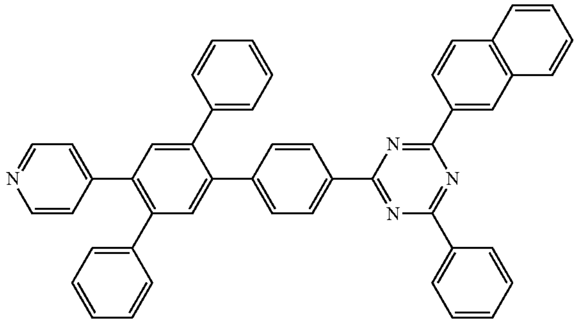
19
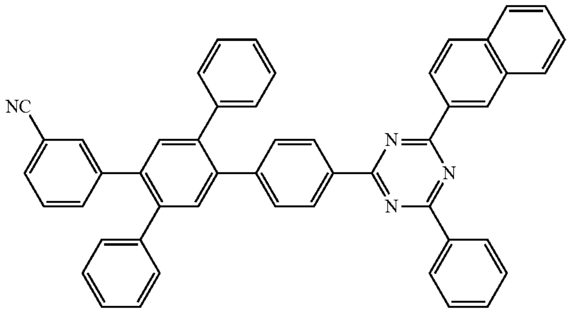
20
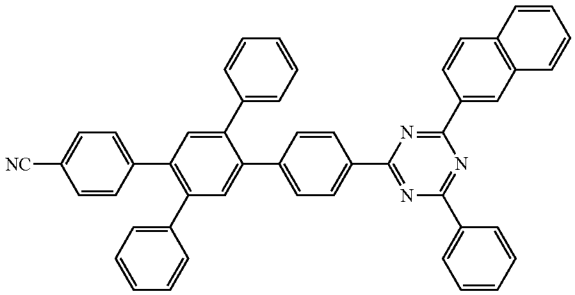
21
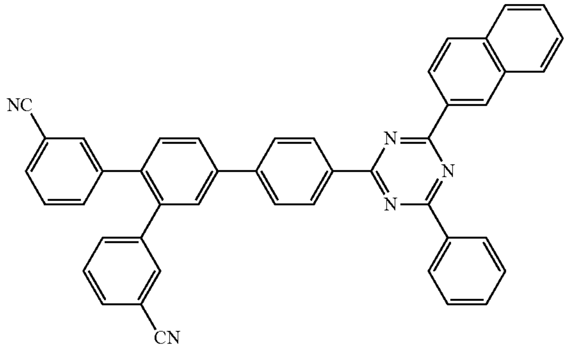
-continued
22
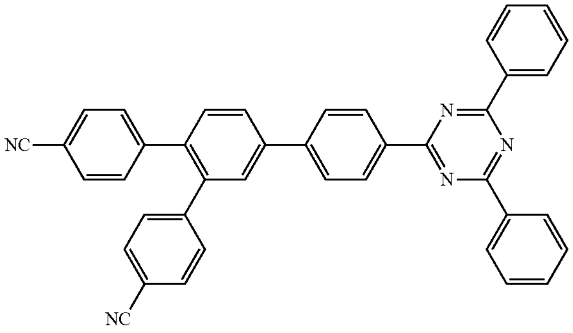
23
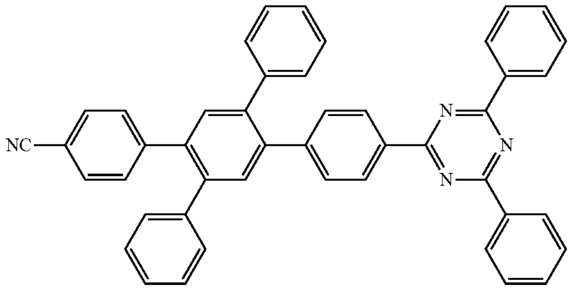
24
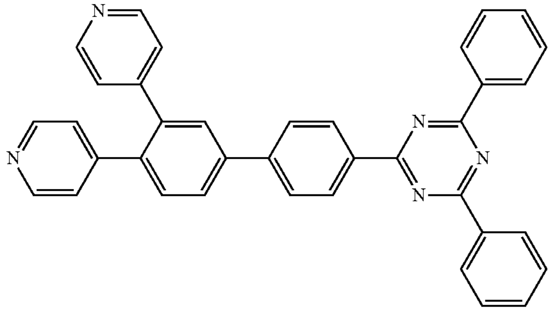
25
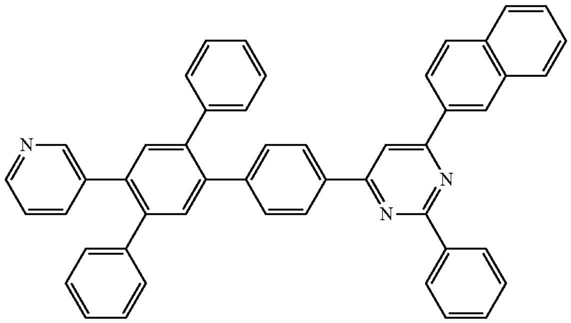

-continued
26
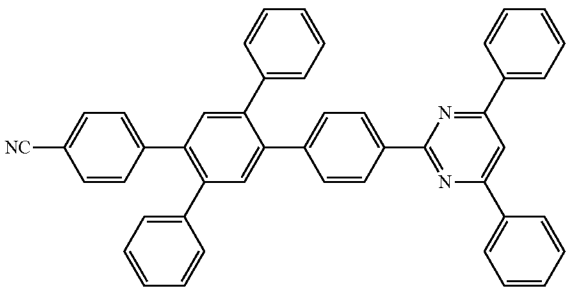
27
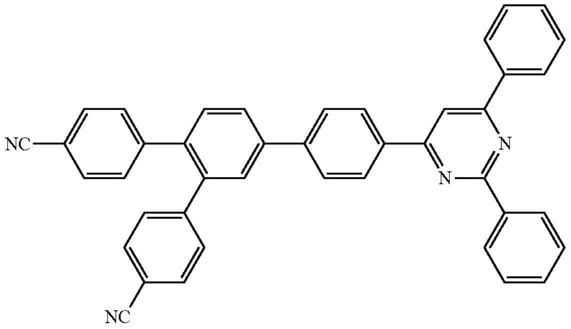
28
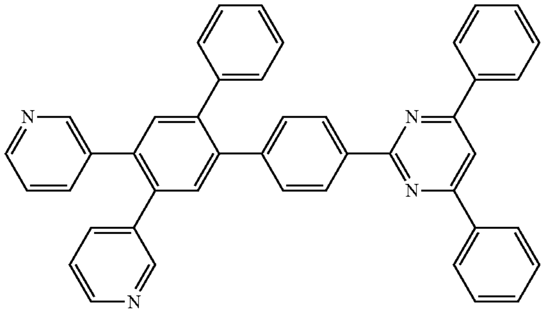
29
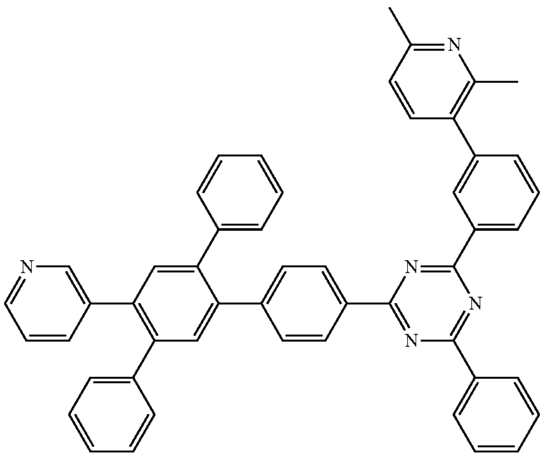
.
In a further embodiment, the compound of Formula (I) is one of the following compounds E1, E2, E3, E4 and E5
E1
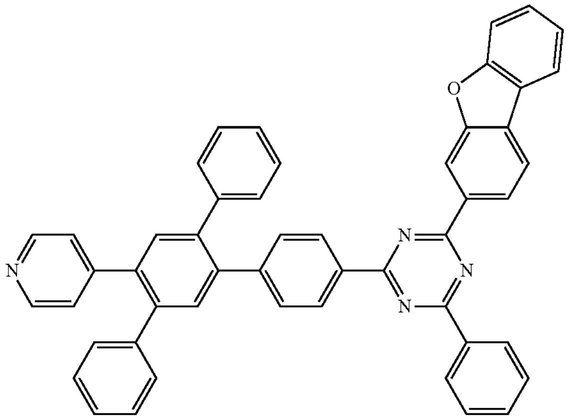
E2
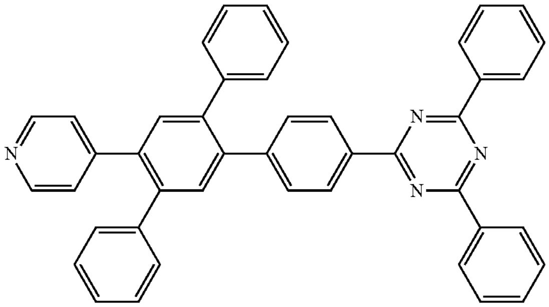
E3
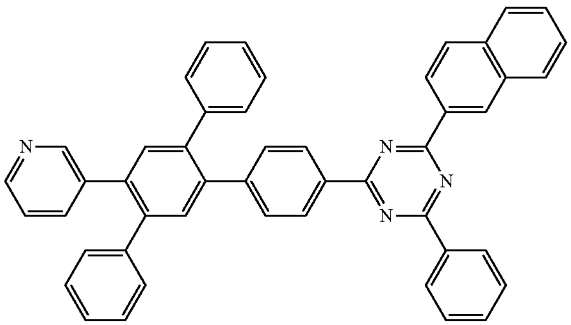
E4
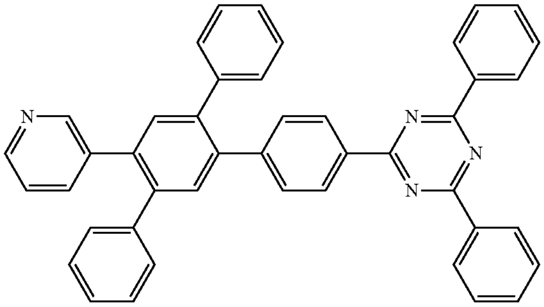

-continued

E5

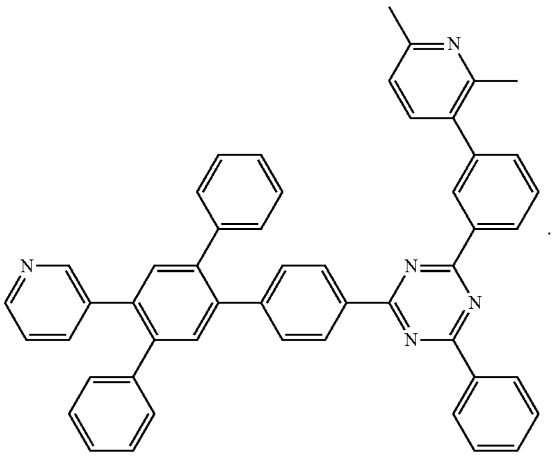

.

The object is further achieved by an organic semiconducting material comprising the compound of Formula (I) as defined herein. In this regard, all modifications and embodiments described above for the compound of Formula (I) are also preferred embodiments of the organic semiconducting material.

The organic semiconducting material may comprise at least one matrix compound and at least one electrical dopant, wherein the matrix compound is the compound of Formula (I). The matrix compound may be an electron transport matrix compound. The electrical dopant may be a n-dopant. The n-dopant may be selected from the group consisting of a metal, a metal salt, a metal complex, a reductive organic radical, and mixtures thereof. The metal may selected from the group consisting of alkali metals, alkaline earth metals, rare earth metals, transition metals of the $4^{th}$ period of the periodic table of elements, and mixtures thereof. The metal salt is an alkali metal salt, an alkaline earth metal salt, or a mixture thereof. The metal complex is an alkali metal complex, an alkaline earth metal complex, or a mixture thereof.

The object is further achieved by an organic electronic device comprising a first electrode, a second electrode and an organic semiconducting layer arranged between the first electrode and the second electrode, wherein the semiconducting layer comprises a compound of Formula (I) as defined herein. In this regard, all modifications and embodiments described above for the compound of Formula (I) are also preferred embodiments of the organic semiconducting device.

In the organic electronic device, wherein the semiconducting layer comprising the compound of Formula (I) may be an electron transport layer, an electron injection layer, a hole blocking layer or an electron generating layer.

The object is further achieved by a display device comprising the inventive organic electronic device. In this regard, all modifications and embodiments described above for the compound of Formula (I) are also preferred embodiments of the display device.

The object is further achieved by the use of the compound of Formula (I) as defined herein for preparing an organic electronic device. In this regard, all modifications and embodiments described above for the compound of Formula (I) are also preferred embodiments of the use.

The object is further achieved by a process for preparing a of compound of Formula (I)

(I)

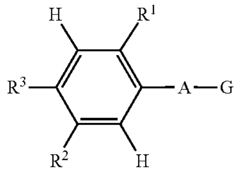

the process comprising reacting a compound of the following Formula (IV) and a compound of the following Formula (V)

(IV)

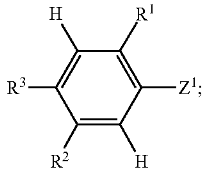

(V)

$Z^2$—A—G, wherein

A is substituted or unsubstituted phenylene, wherein, in case that A is substituted, the one or more substituent(s) are independently selected hydrocarbyl groups;

G is (i) substituted or unsubstituted $C_{10}$ to $C_{60}$ aryl comprising at least two condensed aromatic rings; or (ii) substituted or unsubstituted $C_3$ to $C_{60}$ heteroaryl comprising at least one six-membered ring, wherein the six-membered ring comprises at least two N-atoms; or (iii) substituted or unsubstituted heteroaryl comprising at least two condensed aromatic rings, wherein at least one of the aromatic rings is an azine ring; or (iv) selected from benzofurane, benzothiophene, dibenzothiophene, naphtofurane, naphtothiophene, naphtobenzofurane, naphtobenzothiophene, dinaphtofurane, dinaphtothiophene, xanthene, thioxanthene, dibenzodioxine, phenoxazine, phenothiazine, benzimidazole, benzoxazole, and benzothiazole, wherein the respective group may be unsubstituted or substituted; or (v) selected from fluorene, benzofluorene, dibenzofluorene, naphtofluorene, dinaphtofluorene, benzonaphtofluorene, 9-silafluorene, benzo 9-silafluorene, dibenzo 9-silafluorene, naphto 9-silafluorene, dinaphto 9-silafluorene, and benzonaphto 9-silafluorene;

$R^1$ is (i) H; or (ii) substituted or unsubstituted pyridyl, wherein, in case that $R^1$ is substituted, the one or more substituent(s) are independently selected from the group consisting of $C_1$ to $C_{20}$ aliphatic hydrocarbyl and nitrile; or (iii) substituted or unsubstituted phenyl, wherein, in case that $R^1$ is substituted, the one or more substituent(s) are nitrile; or (iv) a phosphine oxide group;

$R^2$ and $R^3$ are independently (i) substituted or unsubstituted pyridyl, wherein, in case that $R^2$ and/or $R^3$ are substituted, the one or more substituent(s) are independently selected from the group consisting of $C_1$ to $C_{20}$ aliphatic hydrocarbyl and nitrile; or (ii) substituted or unsubstituted phenyl wherein, in case that $R^2$ and/or $R^3$ are substituted, the one or more substituent(s) are independently selected from the group consisting of $C_1$ to $C_{20}$ aliphatic hydrocarbyl and nitrile; or (iii) a phosphine oxide group; and $Z^1$, $Z^2$ are independently selected from the group consisting of halogen, boronic acid, sulfonic acid ester and boronate ester;

with the proviso that at least one of $R^1$, $R^2$ and $R^3$ is (i) substituted or unsubstituted pyridyl, wherein the one or more substituent(s) of the pyridyl, if present, are independently selected from the group consisting of $C_1$ to $C_{20}$ aliphatic hydrocarbyl and nitrile; or (ii) substituted phenyl wherein (a) the one or more substituent(s) of the phenyl are independently selected from the group consisting of $C_1$ to $C_{20}$ aliphatic hydrocarbyl and nitrile, and (b) at least one of the substituents is nitrile; or (iii) a phosphine oxide group.

In this regard, all modifications and embodiments described above for the compound of Formula (I) with respect to the groups A, G, $R^1$, $R^2$ and $R^3$ are also preferred embodiments of the process.

Finally, the object is achieved by compound of Formula (VI) (which is an intermediate of the compound of Formula (I), that is, may be used as a material for preparing the compound of Formula (I))

(VI)

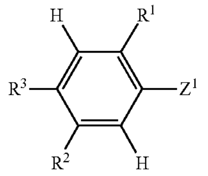

wherein $R^1$ is (i) H; or (ii) substituted or unsubstituted pyridyl, wherein, in case that $R^1$ is substituted, the one or more substituent(s) are independently selected from the group consisting of $C_1$ to $C_{20}$ aliphatic hydrocarbyl and nitrile; or (iii) substituted or unsubstituted phenyl, wherein, in case that $R^1$ is substituted, the one or more substituent(s) are nitrile; or (iv) a phosphine oxide group;

$R^2$ and $R^3$ are independently (i) substituted or unsubstituted pyridyl, wherein, in case that $R^2$ and/or $R^3$ are substituted, the one or more substituent(s) are independently selected from the group consisting of $C_1$ to $C_{20}$ aliphatic hydrocarbyl and nitrile; or (ii) substituted or unsubstituted phenyl wherein, in case that $R^2$ and/or $R^3$ are substituted, the one or more substituent(s) are independently selected from the group consisting of $C_1$ to $C_{20}$ aliphatic hydrocarbyl and nitrile; or (iii) a phosphine oxide group and $Z^1$ is a group selected from halogen, boronic acid group, sulfonic acid ester group and boronate ester group;

with the proviso that at least one of $R^1$, $R^2$ and $R^3$ is (i) substituted or unsubstituted pyridyl, wherein the one or more substituent(s) of the pyridyl, if present, are independently selected from the group consisting of $C_1$ to $C_{20}$ aliphatic hydrocarbyl and nitrile; or (ii) substituted phenyl wherein (a) the one or more substituent(s) of the phenyl are independently selected from the group consisting of $C_1$ to $C_{20}$ aliphatic hydrocarbyl and nitrile, and (b) at least one of the substituents is nitrile; or (iii) a phosphine oxide group.

In this regard, all modifications and embodiments described above for the compound of Formula (I) with respect to the groups $R^1$, $R^2$ and $R^3$ are also preferred embodiments of the compound of Formula (VI).

Advantageous Effects

Surprisingly, it was found that compounds of Formula (I) as defined herein are suitable to improve the voltage stability and lifetime of organic electronic devices such as (blue) OLEDs. In particular, it was found that compounds of Formula (I) can improve both lifetime and voltage stability of an organic light-emitting diode using the same. This effect was found to be even more pronounced for the embodiments referred to herein.

FURTHER EMBODIMENTS

In accordance with the invention, the organic electronic device may comprise, besides the layers already mentioned above, further layers. Exemplary embodiments of respective layers are described in the following:

Substrate

The substrate may be any substrate that is commonly used in manufacturing of, electronic devices, such as organic light-emitting diodes. If light is to be emitted through the substrate, the substrate shall be a transparent or semitransparent material, for example a glass substrate or a transparent plastic substrate. If light is to be emitted through the top surface, the substrate may be both a transparent as well as a non-transparent material, for example a glass substrate, a plastic substrate, a metal substrate or a silicon substrate.

Anode Electrode

Either a first electrode or a second electrode comprised in the inventive organic electronic device may be an anode electrode. The anode electrode may be formed by depositing or sputtering a material that is used to form the anode electrode. The material used to form the anode electrode may be a high work-function material, so as to facilitate hole injection. The anode material may also be selected from a low work function material (i.e. aluminum). The anode electrode may be a transparent or reflective electrode. Transparent conductive oxides, such as indium tin oxide (ITO), indium zinc oxide (IZO), tin-dioxide ($SnO_2$), aluminum zinc oxide (AlZO) and zinc oxide (ZnO), may be used to form the anode electrode. The anode electrode may also be formed using metals, typically silver (Ag), gold (Au), or metal alloys.

Hole Injection Layer

A hole injection layer (HIL) may be formed on the anode electrode by vacuum deposition, spin coating, printing, casting, slot-die coating, Langmuir-Blodgett (LB) deposition, or the like. When the HIL is formed using vacuum deposition, the deposition conditions may vary according to the compound that is used to form the HIL, and the desired structure and thermal properties of the HIL. In general, however, conditions for vacuum deposition may include a deposition temperature of 100° C. to 500° C., a pressure of 10-8 to 10-3 Torr (1 Torr equals 133.322 Pa), and a deposition rate of 0.1 to 10 nm/sec.

When the HIL is formed using spin coating or printing, coating conditions may vary according to the compound that is used to form the HIL, and the desired structure and thermal properties of the HIL. For example, the coating conditions may include a coating speed of about 2000 rpm to about 5000 rpm, and a thermal treatment temperature of about 80° C. to about 200° C. Thermal treatment removes a solvent after the coating is performed.

The HIL may be formed of any compound that is commonly used to form a HIL. Examples of compounds that may be used to form the HIL include a phthalocyanine compound, such as copper phthalocyanine (CuPc), 4,4',4"-tris (3-methylphenylphenylamino) triphenylamine (m-MTDATA), TDATA, 2T-NATA, polyaniline/dodecylbenzenesulfonic acid (Pani/DBSA), poly(3,4-ethylenedioxythiophene)/poly(4-styrenesulfonate) (PEDOT/PSS), polyaniline/camphor sulfonic acid (Pani/CSA), and polyaniline)/poly(4-styrenesulfonate (PANI/PSS).

The HIL may comprise, or consist of, a p-type dopant and the p-type dopant may be selected from tetrafluoro-tetracyanoquinonedimethane (F4TCNQ), 2,2'-(perfluoronaphthalen-2,6-diylidene) dimalononitrile or 2,2',2"-(cyclopropane-1,2,3-triylidene)tris(2-(p-cyanotetrafluorophenyl) acetonitrile) but not limited hereto. The HIL may be selected from a hole-transporting matrix compound doped with a p-type dopant. Typical examples of known doped hole transport materials are: copper phthalocyanine (CuPc), which HOMO level is approximately −5.2 eV, doped with tetrafluoro-tetracyanoquinonedimethane (F4TCNQ), which LUMO level is about −5.2 eV; zinc phthalocyanine (ZnPc) (HOMO=−5.2 eV) doped with F4TCNQ; α-NPD (N,N'-Bis (naphthalen-1-yl)-N,N'-bis(phenyl)-benzidine) doped with F4TCNQ. α-NPD doped with 2,2'-(perfluoronaphthalen-2,6-diylidene) dimalononitrile. The p-type dopant concentrations may be selected from 1 to 20 wt.-%, more preferably from 3 wt.-% to 10 wt.-%.

The thickness of the HIL may be in the range from about 1 nm to about 100 nm, and for example, from about 1 nm to about 25 nm. When the thickness of the HIL is within this range, the HIL may have excellent hole injecting characteristics, without a substantial penalty in driving voltage.

Hole Transport Layer

A hole transport layer (HTL) may be formed on the HIL by vacuum deposition, spin coating, slot-die coating, printing, casting, Langmuir-Blodgett (LB) deposition, or the like. When the HTL is formed by vacuum deposition or spin coating, the conditions for deposition and coating may be similar to those for the formation of the HIL. However, the conditions for the vacuum or solution deposition may vary, according to the compound that is used to form the HTL.

The HTL may be formed of any compound that is commonly used to form a HTL. Compounds that can be suitably used are disclosed for example in Yasuhiko Shirota and Hiroshi Kageyama, Chem. Rev. 2007, 107, 953-1010 and incorporated by reference. Examples of the compound that may be used to form the HTL are: carbazole derivatives, such as N-phenylcarbazole or polyvinylcarbazole; benzidine derivatives, such as N,N'-bis(3-methylphenyl)-N,N'-diphenyl-[1,1-biphenyl]-4,4'-diamine (TPD), or N,N'-di(naphthalen-1-yl)-N,N'-diphenyl benzidine (alpha-NPD); and triphenylamine-based compound, such as 4,4',4"-tris(N-carbazolyl)triphenylamine (TCTA). Among these compounds, TCTA can transport holes and inhibit excitons from being diffused into the EML.

The thickness of the HTL may be in the range of about 5 nm to about 250 nm, preferably, about 10 nm to about 200 nm, further about 20 nm to about 190 nm, further about 40 nm to about 180 nm, further about 60 nm to about 170 nm, further about 80 nm to about 160 nm, further about 100 nm to about 160 nm, further about 120 nm to about 140 nm.

When the thickness of the HTL is within this range, the HTL may have excellent hole transporting characteristics, without a substantial penalty in driving voltage.

Electron Blocking Layer

The function of an electron blocking layer (EBL) is to prevent electrons from being transferred from an emission layer to the hole transport layer and thereby confine electrons to the emission layer. Thereby, efficiency, operating voltage and/or lifetime are improved. Typically, the electron blocking layer comprises a triarylamine compound. The triarylamine compound may have a LUMO level closer to vacuum level than the LUMO level of the hole transport layer. The electron blocking layer may have a HOMO level that is further away from vacuum level compared to the HOMO level of the hole transport layer. The thickness of the electron blocking layer may be selected between 2 and 20 nm.

If the electron blocking layer has a high triplet level, it may also be described as triplet control layer.

The function of the triplet control layer is to reduce quenching of triplets if a phosphorescent green or blue emission layer is used. Thereby, higher efficiency of light emission from a phosphorescent emission layer can be achieved. The triplet control layer is selected from compounds with a triplet level above the triplet level of the phosphorescent emitter in the adjacent emission layer. Suitable compounds for the triplet control layer, in particular the triarylamine compounds, are described in EP 2 722 908 A1.

Emission Layer (EML)

The EML may be formed on the HTL by vacuum deposition, spin coating, slot-die coating, printing, casting, LB deposition, or the like. When the EML is formed using vacuum deposition or spin coating, the conditions for deposition and coating may be similar to those for the formation of the HIL. However, the conditions for deposition and coating may vary, according to the compound that is used to form the EML.

The EML may be formed of a combination of host materials and emitter dopants. The EML may comprise a single host material or a plurality of host materials. The EML may comprise a single emitter dopant or a plurality of emitter dopants. Examples of the host materials are Alq3, 4,4'-N,N'-dicarbazole-biphenyl (CBP), poly(n-vinylcarbazole) (PVK), 9,10-di(naphthalene-2-yl)anthracene (ADN), 4,4',4"-tris(carbazol-9-yl)-triphenylamine (TCTA), 1,3,5-tris(N-phenylbenzimidazole-2-yl)benzene (TPBI), 3-tert-butyl-9,10-di-2-naphthylanthracenee (TBADN), distyrylarylene (DSA) and bis(2-(2-hydroxyphenyl)benzo-thiazolate) zinc (Zn(BTZ)2).

In case the EML comprises a plurality of host materials to form a host mixture the amount of each host material in the mixture of host materials may vary between 0.01 and 99.99 parts by weight.

The emitter dopant may be a phosphorescent or fluorescent emitter. Phosphorescent emitters and emitters which emit light via a thermally activated delayed fluorescence (TADF) mechanism may be preferred due to their higher efficiency. The emitter may be a small molecule or a polymer.

Examples of red emitter dopants are PtOEP, Ir(piq)3, and Btp2lr(acac), but are not limited thereto. These compounds are phosphorescent emitters, however, fluorescent red emitter dopants could also be used.

Examples of phosphorescent green emitter dopants are Ir(ppy)3 (ppy=phenylpyridine), Ir(ppy)2(acac), Ir(mpyp)3.

Examples of phosphorescent blue emitter dopants are F2Irpic, (F2ppy)2Ir(tmd) and Ir(dfppz)3 and ter-fluorene. 4.4'-bis(4-diphenyl amiostyryl)biphenyl (DPAVBi), 2,5,8, 11-tetra-tert-butyl perylene (TBPe) are examples of fluorescent blue emitter dopants.

The amount of the emitter dopant may be in the range from about 0.01 to about 50 parts by weight, based on 100 parts by weight of the host or host mixture. Alternatively, the emission layer may consist of a light-emitting polymer. The EML may have a thickness of about 10 nm to about 100 nm, for example, from about 20 nm to about 60 nm. When the thickness of the EML is within this range, the EML may have excellent light emission, without a substantial penalty in driving voltage.

Hole Blocking Layer (HBL)

A hole blocking layer (HBL) may be formed on the EML, by using vacuum deposition, spin coating, slot-die coating, printing, casting, LB deposition, or the like, in order to prevent the diffusion of holes into the ETL. When the EML comprises a phosphorescent dopant, the HBL may have also a triplet exciton blocking function. The hole blocking layer comprise or consist of the compound of Formula (I) as defined above.

The HBL may also be named auxiliary ETL or a-ETL.

When the HBL is formed using vacuum deposition or spin coating, the conditions for deposition and coating may be similar to those for the formation of the HIL. However, the conditions for deposition and coating may vary, according to the compound that is used to form the HBL. Any compound that is commonly used to form a HBL may be used. Examples of compounds for forming the HBL include oxadiazole derivatives, triazine derivatives, triazole derivatives, and phenanthroline derivatives.

The HBL may have a thickness in the range from about 5 nm to about 100 nm, for example, from about 10 nm to about 30 nm. When the thickness of the HBL is within this range, the HBL may have excellent hole-blocking properties, without a substantial penalty in driving voltage.

Electron Transport Layer (ETL)

The OLED according to the present invention may comprise an electron transport layer (ETL). In accordance with the invention, the electron transport layer may comprise or consist of the compound of Formula (I) as defined herein.

According to various embodiments the OLED may comprise an electron transport layer or an electron transport layer stack comprising at least a first electron transport layer and at least a second electron transport layer.

By suitably adjusting energy levels of particular layers of the ETL, the injection and transport of the electrons may be controlled, and the holes may be efficiently blocked. Thus, the OLED may have long lifetime.

The electron transport layer of the organic electronic device may comprise the compound of Formula (I) as defined above as the organic electron transport matrix (ETM) material. The electron transport layer may comprise, besides the compound of Formula (I), further ETM materials known in the art. Likewise, the electron transport layer may comprise as the only electron transport matrix material the compound of Formula (I). In case that the inventive organic electronic device comprises more than one electron transport layers, the compound of Formula (I) may be comprised in only one of the electron transport layers, in more than one of the electron transport layers or in all of the electron transport layers. In accordance with the invention, the electron transport layer may comprise, besides the ETM material, at least one additive as defined herein.

Further, the electron transport layer may comprise one or more n-type dopants. The additive may be an n-type dopant. The additive can be alkali metal, alkali metal compound, alkaline earth metal, alkaline earth metal compound, transition metal, transition metal compound or a rare earth metal. In another embodiment, the metal can be one selected from a group consisting of Li, Na, K, Rb, Cs, Mg, Ca, Sr, Ba, La, Ce, Sm, Eu, Tb, Dy, and Yb. In another embodiment, the n-type dopant can be one selected from a group consisting of Cs, K, Rb, Mg, Na, Ca, Sr, Eu and Yb. In an embodiment the alkali metal compound may be 8-Hydroxyquinolinolato-lithium (LiQ), Lithium tetra(1H-pyrazol-1-yl)borate or Lithium 2-(diphenylphosphoryl)phenolate. Suitable compounds for the ETM (which may be used in addition to the inventive compound of Formula (I) as defined above) are not particularly limited. In one embodiment, the electron transport matrix compounds consist of covalently bound atoms. Preferably, the electron transport matrix compound comprises a conjugated system of at least 6, more preferably of at least 10 delocalized electrons. In one embodiment, the conjugated system of delocalized electrons may be comprised in aromatic or heteroaromatic structural moieties, as disclosed e.g. in documents EP 1 970 371 A1 or WO 2013/079217 A1.

Electron Injection Layer (EIL)

An optional EIL, which may facilitates injection of electrons from the cathode, may be formed on the ETL, preferably directly on the electron transport layer. Examples of materials for forming the EIL include lithium 8-hydroxyquinolinolate (LiQ), LiF, NaCl, CsF, $Li_2O$, BaO, Ca, Ba, Yb, Mg which are known in the art. Deposition and coating conditions for forming the EIL are similar to those for formation of the HIL, although the deposition and coating conditions may vary, according to the material that is used to form the EIL. The EIL may be the organic semiconducting layer comprising or consisting of the compound of Formula (I).

The thickness of the EIL may be in the range from about 0.1 nm to about 10 nm, for example, in the range from about 0.5 nm to about 9 nm. When the thickness of the EIL is within this range, the EIL may have satisfactory electron-injecting properties, without a substantial penalty in driving voltage.

Cathode Electrode

The cathode electrode is formed on the EIL, if present. The cathode electrode may be formed of a metal, an alloy, an electrically conductive compound, or a mixture thereof. The cathode electrode may have a low work function. For example, the cathode electrode may be formed of lithium (Li), magnesium (Mg), aluminum (Al), aluminum (Al)-lithium (Li), calcium (Ca), barium (Ba), ytterbium (Yb), magnesium (Mg)-indium (In), magnesium (Mg)-silver (Ag), or the like. Alternatively, the cathode electrode may be formed of a transparent conductive oxide, such as ITO or IZO.

The thickness of the cathode electrode may be in the range from about 5 nm to about 1000 nm, for example, in the range from about 10 nm to about 100 nm. When the thickness of the cathode electrode is in the range from about 5 nm to about 50 nm, preferably in the range from about 7 nm to about 20 nm, more preferably in the range from about 9 nm to about 15 nm, the cathode electrode may be transparent or semitransparent even if formed by a metal or metal alloy.

It is to be understood that the cathode electrode is not part of an electron injection layer or the electron transport layer.

Charge Generation Layer

The charge generation layer (CGL) may comprise a p-type and an n-type layer. An interlayer may be arranged between the p-type layer and the n-type layer. The CGL may comprise or consist of the compound of Formula (I).

Typically, the charge generation layer is a pn junction joining an n-type charge generation layer (electron generating layer) and a hole generating layer. The n-side of the pn junction generates electrons and injects them into the layer which is adjacent in the direction to the anode. Analogously, the p-side of the p-n junction generates holes and injects them into the layer which is adjacent in the direction to the cathode.

Charge generating layers may be used in tandem devices, for example, in tandem OLEDs comprising, between two electrodes, two or more emission layers. In a tandem OLED comprising two emission layers, the n-type charge generation layer provides electrons for the first light emission layer arranged near the anode, while the hole generating layer provides holes to the second light emission layer arranged between the first emission layer and the cathode.

Suitable matrix materials for the hole generating layer may be materials conventionally used as hole injection and/or hole transport matrix materials. Also, p-type dopant used for the hole generating layer can employ conventional materials. For example, the p-type dopant can be one selected from a group consisting of tetrafluoro-7,7,8,8-tetracyanoquinodimethane (F4-TCNQ), derivatives of tetracyanoquinodimethane, radialene derivatives, iodine, $FeCl3$, $FeF3$, and $SbCl5$. Also, the host can be one selected from a group consisting of N,N'-di(naphthalen-1-yl)-N,N-diphenyl-benzidine (NPB), N,N'-diphenyl-N,N'-bis(3-methylphenyl)-1,1-biphenyl-4,4'-diamine (TPD) and N,N',N'-tetranaphthyl-benzidine (TNB). The p-type charge generation layer may consist of CNHAT.

The n-type charge generating layer may be the layer comprising the compound of Formula (I). The n-type charge generation layer can be layer of a neat n-type dopant, for example of an electropositive metal, or can consist of an organic matrix material doped with the n-type dopant. In one embodiment, the n-type dopant can be alkali metal, alkali metal compound, alkaline earth metal, alkaline earth metal compound, a transition metal, a transition metal compound or a rare earth metal. In another embodiment, the metal can be one selected from a group consisting of Li, Na, K, Rb, Cs, Mg, Ca, Sr, Ba, La, Ce, Sm, Eu, Tb, Dy, and Yb. More specifically, the n-type dopant can be one selected from a group consisting of Cs, K, Rb, Mg, Na, Ca, Sr, Eu and Yb. Suitable matrix materials for the electron generating layer may be the materials conventionally used as matrix materials for electron injection or electron transport layers. The matrix material can be for example one selected from a group consisting of triazine compounds, hydroxyquinoline derivatives like tris(8-hydroxyquinoline)aluminum, benzazole derivatives, and silole derivatives.

The hole generating layer is arranged in direct contact to the n-type charge generation layer.

Organic Light-Emitting Diode (OLED)

The organic electronic device according to the invention may be an organic light-emitting device.

According to one aspect of the present invention, there is provided an organic light-emitting diode (OLED) comprising: a substrate; an anode electrode formed on the substrate; a hole injection layer, a hole transport layer, an emission layer, an organic semiconducting layer comprising a compound of Formula (I) or consisting of a compound of Formula (I) and a cathode electrode.

According to another aspect of the present invention, there is provided an OLED comprising: a substrate; an anode electrode formed on the substrate; a hole injection layer, a hole transport layer, an electron blocking layer, an emission layer, a hole blocking layer, an organic semiconducting layer comprising a compound of Formula (I) or consisting of a compound of Formula (I) and a cathode electrode.

According to another aspect of the present invention, there is provided an OLED comprising: a substrate; an anode electrode formed on the substrate; a hole injection layer, a hole transport layer, an electron blocking layer, an emission layer, a hole blocking layer, an organic semiconducting layer comprising a compound of Formula (I) or consisting of a compound of Formula (I), an electron injection layer, and a cathode electrode.

According to various embodiments of the present invention, there may be provided OLEDs layers arranged between the above mentioned layers, on the substrate or on the top electrode.

According to one aspect, the OLED can comprise a layer structure of a substrate that is adjacently arranged to an anode electrode, the anode electrode is adjacently arranged to a first hole injection layer, the first hole injection layer is adjacently arranged to a first hole transport layer, the first hole transport layer is adjacently arranged to a first electron blocking layer, the first electron blocking layer is adjacently arranged to a first emission layer, the first emission layer is adjacently arranged to a first electron transport layer, the first electron transport layer is adjacently arranged to an n-type charge generation layer, the n-type charge generation layer is adjacently arranged to a hole generating layer, the hole generating layer is adjacently arranged to a second hole transport layer, the second hole transport layer is adjacently arranged to a second electron blocking layer, the second electron blocking layer is adjacently arranged to a second emission layer, between the second emission layer and the cathode electrode an optional electron transport layer and/or an optional injection layer are arranged.

The organic semiconducting layer according to the invention may be an emission layer, a hole blocking layer, an electron transport layer, a first electron transport layer, a n-type charge generation layer and/or a second electron transport layer.

For example, the OLED (100) according to FIG. 2 may be formed by a process, wherein on a substrate (110), an anode (120), a hole injection layer (130), a hole transport layer (140), an electron blocking layer (145), an emission layer (150), a hole blocking layer (155), an electron transport layer (160), an electron injection layer (180) and the cathode electrode (190) are subsequently formed in that order.

Organic Electronic Device

An organic electronic device according to the invention comprises an organic semiconducting layer comprising a compound of Formula (I) or consisting of a compound of Formula (I).

An organic electronic device according to one embodiment may include a substrate, an anode layer, an organic semiconducting layer comprising a compound of Formula (I) or consisting of a compound of Formula (I) and a cathode layer.

An organic electronic device according to one embodiment comprises at least one organic semiconducting layer comprising at least one compound (I) or consisting of a compound of Formula (I), at least one anode layer, at least one cathode layer and at least one emission layer, wherein the organic semiconducting layer is preferably arranged between the emission layer and the cathode layer.

An organic light-emitting diode (OLED) according to the invention may include an anode, a hole transport layer (HTL), an emission layer (EML), an electron transport layer (ETL) comprising at least one compound of Formula (I), and a cathode, which are sequentially stacked on a substrate. In this regard, the HTL, the EML, and the ETL are thin films formed from organic compounds.

An organic electronic device according to one embodiment can be a light emitting device, thin film transistor, a charge storage device, a display device or a photovoltaic cell, and preferably a light emitting device.

According to another aspect of the present invention, there is provided a method of manufacturing an organic electronic device, the method using:

- at least one deposition source, preferably two deposition sources and more preferred at least three deposition sources.

The methods for deposition that can be suitable comprise:

- deposition via vacuum thermal evaporation;
- deposition via solution processing, preferably the processing is selected from spin-coating, printing, casting; and/or
- slot-die coating.

According to various embodiments of the present invention, there is provided a method using:

- a first deposition source to release the compound (I) according to the invention, and
- a second deposition source to release a metal, a metal complex, an organo-metallic compound, a metal salt or an alkali or alkaline earth metal complex; alternatively an organic alkali or alkaline earth metal complex; alternatively 8-hydroxyquinolinolato lithium or alkali borate;

the method comprising the steps of forming the organic semiconducting layer; whereby for an organic light-emitting diode (OLED):

- the organic semiconducting layer is formed by releasing the compound (I) according to the invention from the first deposition source and a metal, a metal complex, an organo-metallic compound, a metal salt or an alkali or alkaline earth metal complex; alternatively an organic alkali or alkaline earth metal complex; alternatively 8-hydroxyquinolinolato lithium or alkali borate, from the second deposition source.

According to various embodiments of the present invention, the method may further include forming on the anode electrode, an emission layer and at least one layer selected from the group consisting of forming a hole injection layer, forming a hole transport layer, or forming a hole blocking layer, between the anode electrode and the first electron transport layer.

According to various embodiments of the present invention, the method may further include the steps for forming an organic light-emitting diode (OLED), wherein

- on a substrate a first anode electrode is formed,
- on the first anode electrode an emission layer is formed,
- on the emission layer an electron transport layer stack is formed, optionally a hole blocking layer is formed on the emission layer and an organic semiconducting layer is formed,
- and finally a cathode electrode is formed,
- optionally a hole injection layer, a hole transport layer, and a hole blocking layer, formed in that order between the first anode electrode and the emission layer,
- optionally an electron injection layer is formed between the organic semiconducting layer and the cathode electrode.

According to various embodiments of the present invention, the method may further comprise forming an electron injection layer on the organic semiconducting layer. However, according to various embodiments of the OLED of the present invention, the OLED may not comprise an electron injection layer.

According to various embodiments, the OLED may have the following layer structure, with the layers having the following order:

- anode, hole injection layer, first hole transport layer, second hole transport layer, emission layer, optional hole blocking layer, organic semiconducting layer comprising a compound (I) according to the invention, optional electron injection layer, and cathode, or
- anode, hole injection layer, first hole transport layer, second hole transport layer, organic semiconducting layer comprising a compound (I) according to the invention, optional hole blocking layer, first electron transport layer, optional electron injection layer, and cathode, or
- anode, hole injection layer, first hole transport layer, second hole transport layer, emission layer, organic semiconducting layer comprising a compound (I) according to the invention, first electron transport layer, optional electron injection layer, and cathode.

According to another aspect of the invention, it is provided an electronic device comprising at least one organic light emitting device according to any embodiment described throughout this application, preferably, the electronic device comprises the organic light emitting diode in one of embodiments described throughout this application. More preferably, the electronic device is a display device.

In one embodiment, the organic electronic device according to the invention comprising an organic semiconducting layer comprising a compound (I) or consisting of a compound (I) may further comprise a layer comprising a radialene compound and/or a quinodimethane compound.

In one embodiment, the radialene compound and/or the quinodimethane compound may be substituted with one or more halogen atoms and/or with one or more electron withdrawing groups. Electron withdrawing groups can be selected from nitrile groups, halogenated alkyl groups, alternatively from perhalogenated alkyl groups, alternatively from perfluorinated alkyl groups. Other examples of electron withdrawing groups may be acyl, sulfonyl groups or phosphoryl groups.

Alternatively, acyl groups, sulfonyl groups and/or phosphoryl groups may comprise halogenated and/or perhalogenated hydrocarbyl. In one embodiment, the perhalogenated hydrocarbyl may be a perfluorinated hydrocarbyl. Examples of a perfluorinated hydrocarbyl can be perfluormethyl, perfluorethyl, perfluorpropyl, perfluorisopropyl, perfluorobutyl, perfluorophenyl, perfluorotolyl; examples of sulfonyl groups comprising a halogenated hydrocarbyl may be trifluoromethylsulfonyl, pentafluoroethylsulfonyl, pentafluorophenylsulfonyl, heptafluoropropylsufonyl, nonafluorobutylsulfonyl, and like.

In one embodiment, the radialene and/or the quinodimethane compound may be comprised in a hole injection, hole transporting and/or a hole generation layer.

In one embodiment, the radialene compound may have Formula (XX) and/or the quinodimethane compound may have Formula (XXIa) or (XXIb):

(XX)

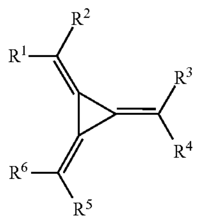

(XXIa)

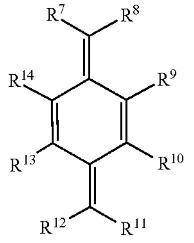

(XXIb)

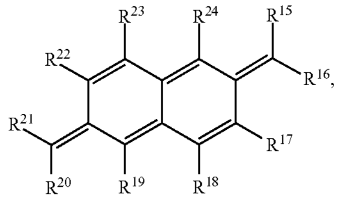

wherein $R^1$, $R^2$, $R^3$, $R^4$, $R^5$, $R^6$, $R^7$, $R^8$, $R^{11}$, $R^{12}$, $R^{15}$, $R^{16}$, $R^{20}$, $R^{21}$ are independently selected from above mentioned electron withdrawing groups and $R^9$, $R^{10}$, $R^{13}$, $R^{14}$, $R^{17}$, $R^{18}$, $R^{19}$, $R^{22}$, $R^{23}$ and $R^{24}$ are independently selected from H, halogen and above mentioned electron withdrawing groups.

General Definitions

In the present specification, when a definition is not otherwise provided, an "alkyl group" may refer to an aliphatic hydrocarbon group. The alkyl group may refer to "a saturated alkyl group" without any double bond or triple bond. The term "alkyl" as used herein shall encompass linear as well as branched and cyclic alkyl. For example, $C_3$-alkyl may be selected from n-propyl and iso-propyl. Likewise, $C_4$-alkyl encompasses n-butyl, sec-butyl and t-butyl. Likewise, $C_6$-alkyl encompasses n-hexyl and cyclohexyl.

The subscribed number n in $C_n$ relates to the total number of carbon atoms in the respective alkyl, arylene, heteroarylene or aryl group.

The term "aryl" or "arylene" as used herein shall encompass phenyl ($C_6$-aryl), fused aromatics, such as naphthalene, anthracene, phenanthrene, tetracene etc. Further encompassed are biphenyl and oligo- or polyphenyls, such as terphenyl etc. Further encompassed shall be any further aromatic hydrocarbon substituents, such as fluorenyl etc. "Arylene" respectively "heteroarylene", refers to groups to which two further moieties are attached. In the present specification the term "aryl group" or "arylene group" may refer to a group comprising at least one hydrocarbon aromatic moiety, and all the elements of the hydrocarbon aromatic moiety may have p-orbitals which form conjugation, for example a phenyl group, a naphtyl group, an anthracenyl group, a phenanthrenyl group, a pyrenyl group, a fluorenyl group and the like. The aryl or arylene group may include a monocyclic or fused ring polycyclic (i.e., rings sharing adjacent pairs of carbon atoms) functional group.

The term "hydrocarbyl" as used herein refers to an univalent radical derived from a hydrocarbon (comprising only C and H), such as alkyl, aryl, cycloalkyl, alkenyl, alkynyl etc.

The term "heteroaryl" as used herein refers to aryl groups in which at least one carbon atom is substituted with a heteroatom, preferably selected from N, O, S, B or Si. The term "heteroaryl" as used herein does not encompass heterocyclic groups that lack aromaticity in the heterocycle. That is, a compound comprising one or more aromatic non-heterocyclic rings and a heterocyclic ring fused to the aromatic non-heterocyclic ring(s) is not a heteroaryl group in terms of the present disclosure if the heterocyclic ring is not aromatic. Examples of such heterocyclic groups which are not a heteroaryl in terms of the present disclosure can be partially saturated heterocyclic rings as for example the non-aromatic six-membered aza-heterocycle comprised in dihydroacridine or fully saturated six-membered heterocycle in morpholine.

The subscripted number n in $C_n$-heteroaryl merely refers to the number of carbon atoms excluding the number of heteroatoms. In this context, it is clear that a $C_3$ heteroarylene group is an aromatic compound comprising three carbon atoms, such as pyrazole, imidazole, oxazole, thiazole and the like.

The term "heteroaryl" may refer to aromatic heterocycles with at least one heteroatom, and all the elements of the hydrocarbon heteroaromatic moiety may have p-orbitals which form conjugation. The heteroatom may be selected from N, O, S, B, Si, P, Se, preferably from N, O and S. A heteroarylene ring may comprise at least 1 to 3 heteroatoms. Preferably a heteroarylene ring may comprise at least 1 to 3 heteroatoms individually selected from N, S and/or O.

The term "heteroaryl" as used herewith shall encompass pyridine, quinoline, quinazoline, pyridine, triazine, benzimidazole, benzothiazole, benzo[4,5]thieno[3,2-d]pyrimidine, carbazole, xanthene, phenoxazine, benzoacridine, dibenzoacridine and the like.

An azine as used herein is a heterocyclic compound containing a 6-membered N-containing aromatic ring. It is an analog of a benzene ring in which one or more of the carbon atoms has been replaced by a nitrogen atom. Exemplary azines are pyridine, pyridazine, pyrimidine, pyrazine, triazine and tetrazine.

In the present specification, the single bond refers to a direct bond.

The term "fluorinated" as used herein refers to a hydrocarbon group in which at least one of the hydrogen atoms comprised in the hydrocarbon group is substituted by a fluorine atom. Fluorinated groups in which all of the hydrogen atoms thereof are substituted by fluorine atoms are referred to as perfluorinated groups and are particularly addressed by the term "fluorinated".

In terms of the invention, a group is "substituted with" another group if one of the hydrogen atoms comprised in this group is replaced by another group, wherein the other group is the substituent.

In terms of the invention, the expression "between" with respect to one layer being between two other layers does not exclude the presence of further layers which may be arranged between the one layer and one of the two other layers. In terms of the invention, the expression "in direct contact" with respect to two layers being in direct contact with each other means that no further layer is arranged between those two layers. One layer deposited on the top of another layer is deemed to be in direct contact with this layer.

With respect to the inventive organic semiconducting layer as well as with respect to the inventive compound, the compounds mentioned in the experimental part are most preferred.

The inventive organic electronic device may be an organic electroluminescent device (OLED) an organic photovoltaic device (OPV), a lighting device, or an organic field-effect transistor (OFET). A lighting device may be any of the devices used for illumination, irradiation, signaling, or projection. They are correspondingly classified as illuminating, irradiating, signaling, and projecting devices. A lighting device usually consists of a source of optical radiation, a device that transmits the radiant flux into space in the desired direction, and a housing that joins the parts into a single device and protects the radiation source and light-transmitting system against damage and the effects of the surroundings.

According to another aspect, the organic electroluminescent device according to the present invention may comprise more than one emission layer, preferably two or three emission layers. An OLED comprising more than one emission layer is also described as a tandem OLED or stacked OLED.

The organic electroluminescent device (OLED) may be a bottom- or top-emission device.

Another aspect is directed to a device comprising at least one organic electroluminescent device (OLED).

A device comprising organic light-emitting diodes is for example a display or a lighting panel.

In the present invention, the following defined terms, these definitions shall be applied, unless a different definition is given in the claims or elsewhere in this specification.

In the context of the present specification the term "different" or "differs" in connection with the matrix material means that the matrix material differs in their structural Formula.

The terms "OLED" and "organic light-emitting diode" are simultaneously used and have the same meaning. The term "organic electroluminescent device" as used herein may comprise both organic light emitting diodes as well as organic light emitting transistors (OLETs).

As used herein, "weight percent", "wt.-%", "percent by weight", "% by weight", parts by weight and variations thereof refer to a composition, component, substance or agent as the weight of that component, substance or agent of the respective electron transport layer divided by the total weight of the respective electron transport layer thereof and multiplied by 100. It is under-stood that the total weight percent amount of all components, substances and agents of the respective electron transport layer and electron injection layer are selected such that it does not exceed 100 wt.-%.

As used herein, "volume percent", "vol.-%", "percent by volume", "% by volume", and variations thereof refer to a composition, component, substance or agent as the volume of that component, substance or agent of the respective electron transport layer divided by the total volume of the respective electron transport layer thereof and multiplied by 100. It is understood that the total volume percent amount of all components, substances and agents of the cathode layer are selected such that it does not exceed 100 vol.-%.

All numeric values are herein assumed to be modified by the term "about", whether or not explicitly indicated. As used herein, the term "about" refers to variation in the numerical quantity that can occur. Whether or not modified by the term "about" the claims include equivalents to the quantities.

It should be noted that, as used in this specification and the appended claims, the singular forms "a", "an", and "the" include plural referents unless the content clearly dictates otherwise.

The term "free of", "does not contain", "does not comprise" does not exclude impurities. Impurities have no technical effect with respect to the object achieved by the present invention.

In the context of the present specification the term "essentially non-emissive" or "non-emissive" means that the contribution of the compound or layer to the visible emission spectrum from the device is less than 10%, preferably less than 5% relative to the visible emission spectrum. The visible emission spectrum is an emission spectrum with a wavelength of about ≥380 nm to about ≤780 nm.

Preferably, the organic semiconducting layer comprising the compound (I) is essentially non-emissive or non-emitting.

The operating voltage, also named U, is measured in Volt (V) at 10 milliAmpere per square centimeter (mA/cm2).

The candela per Ampere efficiency, also named cd/A efficiency is measured in candela per ampere at 10 milliAmpere per square centimeter (mA/cm2).

The external quantum efficiency, also named EQE, is measured in percent (%).

The color space is described by coordinates CIE-x and CIE-y (International Commission on Illumination 1931). For blue emission the CIE-y is of particular importance. A smaller CIE-y denotes a deeper blue color.

The highest occupied molecular orbital, also named HOMO, and lowest unoccupied molecular orbital, also named LUMO, are measured in electron volt (eV).

The term "OLED", "organic light emitting diode", "organic light emitting device", "organic optoelectronic device" and "organic light-emitting diode" are simultaneously used and have the same meaning.

The term "life-span" and "lifetime" are simultaneously used and have the same meaning.

The anode electrode and cathode electrode may be described as anode electrode/cathode electrode or anode electrode/cathode electrode or anode electrode layer/cathode electrode layer.

Room temperature, also named ambient temperature, is 23° C.

DESCRIPTION OF THE DRAWINGS

These and/or other aspects and advantages of the present invention will become apparent and more readily appreciated from the following description of the exemplary embodiments, taken in conjunction with the accompanying drawings, of which.

DETAILED DESCRIPTION

Figure 1:
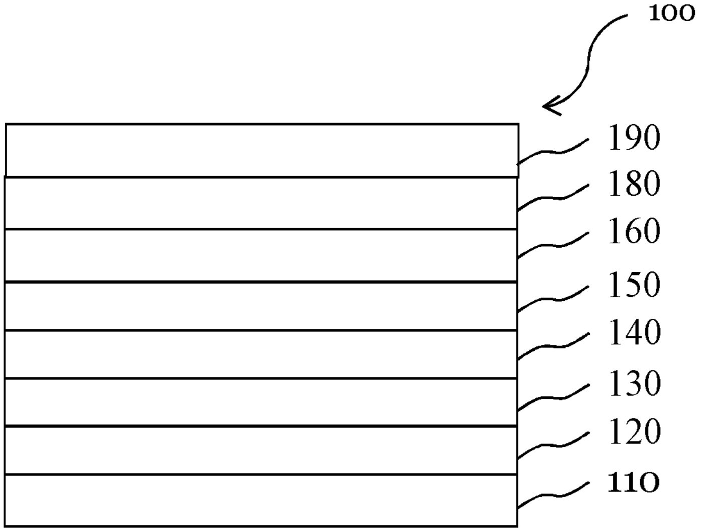
FIG. 1 is a schematic sectional view of an organic light-emitting diode (OLED), according to an exemplary embodiment of the present invention.

Reference will now be made in detail to the exemplary embodiments of the present invention, examples of which are illustrated in the accompanying drawings, wherein like reference numerals refer to the like elements throughout. The exemplary embodiments are described below, in order to explain the aspects of the present invention, by referring to the figures.

Herein, when a first element is referred to as being formed or disposed "on" or "onto" a second element, the first element can be disposed directly on the second element, or one or more other elements may be disposed there between. When a first element is referred to as being formed or disposed "directly on" or "directly onto" a second element, no other elements are disposed there between.

FIG. 1 is a schematic sectional view of an organic light-emitting diode (OLED) 100, according to an exemplary embodiment of the present invention. The OLED 100 includes a substrate 110, an anode 120, a hole injection layer (HIL) 130, a hole transport layer (HTL) 140, an emission layer (EML) 150, an electron transport layer (ETL) 160. The electron transport layer (ETL) 160 is formed on the EML 150. Onto the electron transport layer (ETL) 160, an electron injection layer (EIL) 180 is disposed. The cathode 190 is disposed directly onto the electron injection layer (EIL) 180.

Instead of a single electron transport layer **16*o***, optionally an electron transport layer stack (ETL) can be used.

Figure 2:
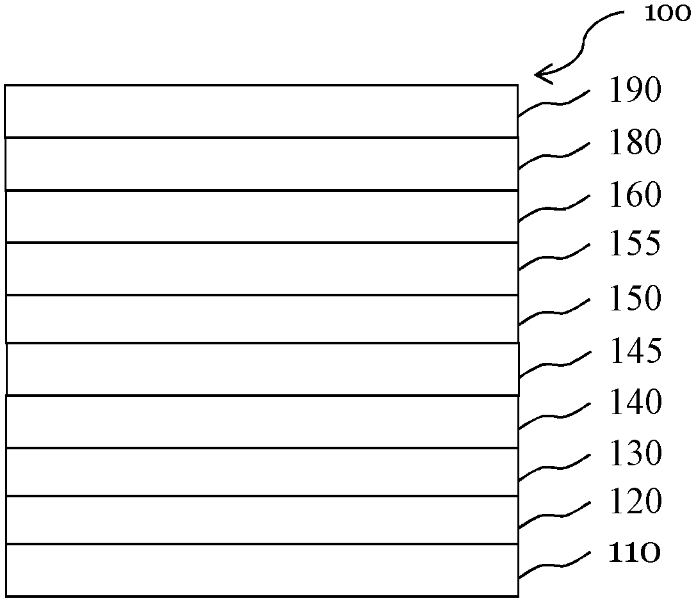
FIG. 2 is a schematic sectional view of an OLED, according to an exemplary embodiment of the present invention.

FIG. 2 is a schematic sectional view of an OLED 100, according to another exemplary embodiment of the present invention. FIG. 2 differs from FIG. 1 in that the OLED 100 of FIG. 2 comprises an electron blocking layer (EBL) 145 and a hole blocking layer (HBL) 155.

Referring to FIG. 2, the OLED 100 includes a substrate **11*o*, an anode 120, a hole injection layer (HIL) 130, a hole transport layer (HTL) 140, an electron blocking layer (EBL) 145, an emission layer (EML) 150, a hole blocking layer (HBL) 155, an electron transport layer (ETL) 160, an electron injection layer (EIL) 180 and a cathode electrode 190**.

Preferably, the organic semiconducting layer comprising a compound (I) or consisting of a compound (I) may be an EML, an HBL or an ETL.

Figure 3:
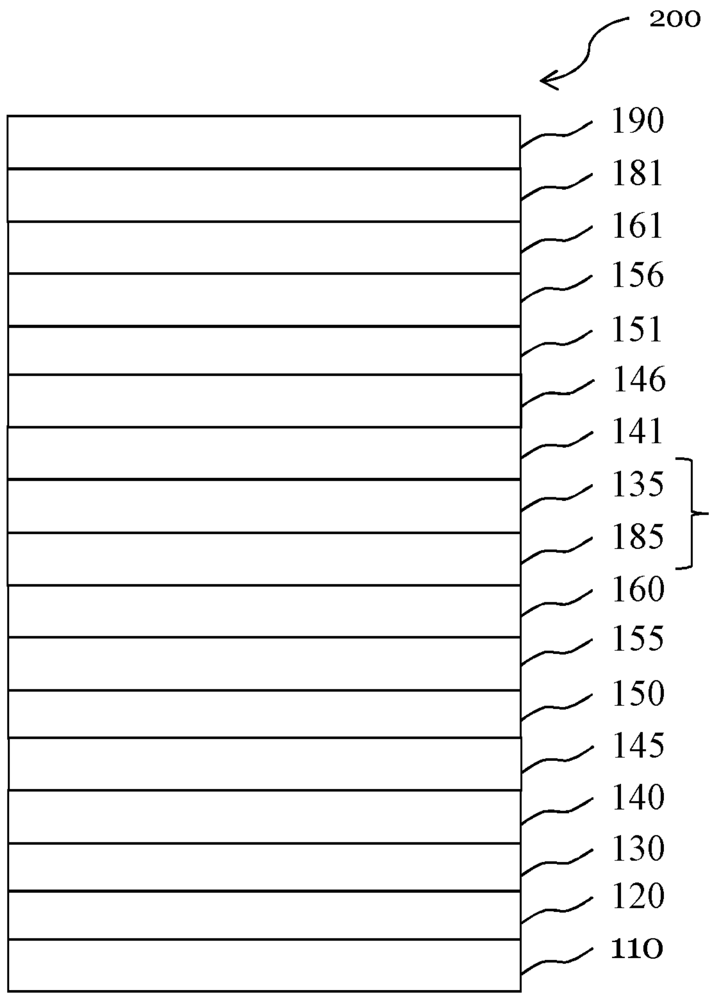
FIG. 3 is a schematic sectional view of a tandem OLED comprising a charge generation layer, according to an exemplary embodiment of the present invention.

FIG. 3 is a schematic sectional view of a tandem OLED 200, according to another exemplary embodiment of the present invention. FIG. 3 differs from FIG. 2 in that the OLED 200 of FIG. 3 further comprises a charge generation layer (CGL) and a second emission layer (151).

Referring to FIG. 3, the OLED 200 includes a substrate no, an anode 120, a first hole injection layer (HIL) 130, a first hole transport layer (HTL) 140, a first electron blocking layer (EBL) 145, a first emission layer (EML) **15*o*, a first hole blocking layer (HBL) 155, a first electron transport layer (ETL) 160, an n-type charge generation layer (n-type CGL) 185, a hole generating layer (p-type charge generation layer; p-type GCL) 135, a second hole transport layer (HTL) 141, a second electron blocking layer (EBL) 146, a second emission layer (EML) 151, a second hole blocking layer (EBL) 156, a second electron transport layer (ETL) 161, a second electron injection layer (EIL) 181 and a cathode 190**.

Preferably, the organic semiconducting layer comprising a compound (I) or consisting of a compound (I) may be the first EML, first HBL, first ETL, n-type CGL and/or second EML, second HBL, second ETL.

While not shown in FIG. 1, FIG. 2 and FIG. 3, a sealing layer may further be formed on the cathode electrodes 190, in order to seal the OLEDs 100 and 200. In addition, various other modifications may be applied thereto.

DETAILED DESCRIPTION

Hereinafter, the embodiments are illustrated in more detail with reference to examples. However, the present disclosure is not limited to the following examples. Reference will now be made in detail to the exemplary aspects.

Synthesis of Compounds

The abbreviations used in synthesis procedures have the following meaning:

Et is ethyl, Ph is phenyl, Ac is acetyl, Tf is trifloromethylsulfonyl, EtOAc is ethyl acetate, DCM is dichloromethane, THF is tetrahydrofuran, $Tf_2O$ is trifluoromethane sulfonic acid anhydride, SPhos is 2-dicyclohexylphosphino-2',6'-dimethoxybiphenyl, dppf is 1,1'-ferrocenediyl-bis (diphenylphosphine), APCI is atmospheric pressure chemical ionization, ESI is electrospray ionization, MS is mass spectrometry.

Synthesis of Intermediates 3-(5'-bromo-[1,1':4',1"-terphenyl]-2'-yl)pyridine

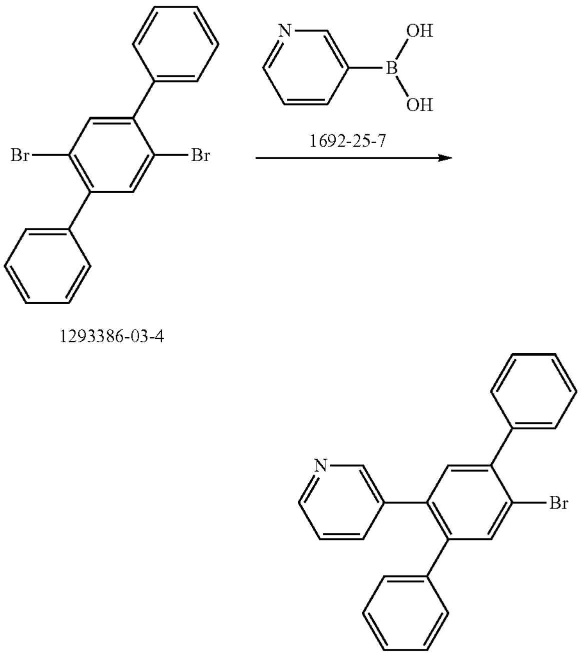

A flask was flushed with argon and charged with 2',5'-dibromo-1,1':4',1"-terphenyl (57.7 g, 148.7 mmol), pyridin-3-ylboronic acid (24.3 g, 148.7 mmol), $Pd(OAc)_2$ (1.7 g, 7.4 mmol), $PPh_3$ (7.8 g, 29.7 mmol) and $K_3PO_4$ (63.1 g, 297.4 mmol). A mixture of deaerated 1,4-dioxane/water (3:1, 1.1 L) was added and the reaction mixture was heated to 82° C.

under an argon atmosphere for 26 h. After cooling down to room temperature, the crude product was extracted with a DCM/aqueous $K_2CO_3$ mixture, the extract evaporated under reduced pressure and dried. Further purification was achieved via silica gel column chromatography and recrystallization from petroleum ether/DCM (20:1, 158 mL) to yield 28.1 g (49%) of a white solid after drying.

APCI-MS: m/z=384 ([M−H]$^+$).

4-(5'-bromo-[1,1':4',1"-terphenyl]-2'-yl)pyridine

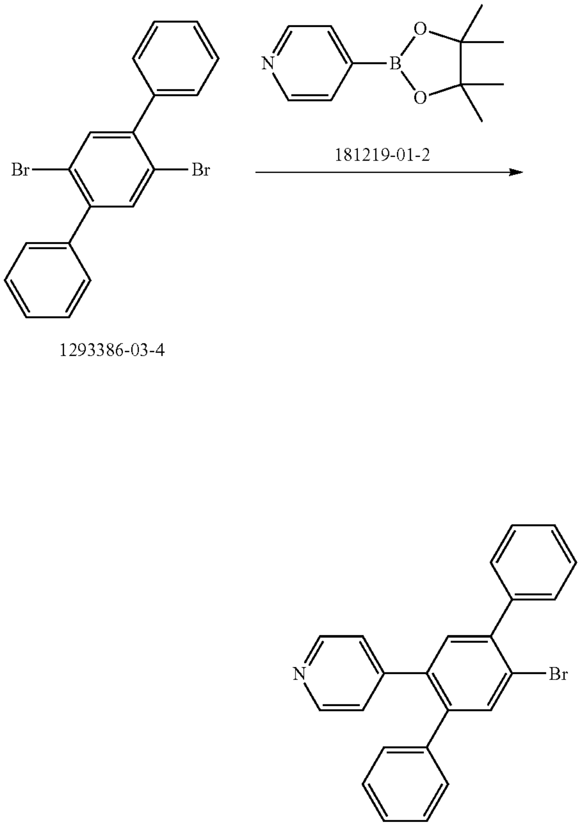

A flask was flushed with argon and charged with 2',5'-dibromo-1,1':4',1"-terphenyl (40.4 g, 104.1 mmol), 4-(4,4,5,5-tetramethyl-1,3,2-dioxaborolan-2-yl)pyridine (21.8 g, 104.1 mmol), $Pd(OAc)_2$ (1.2 g, 5.2 mmol), $PPh_3$ (5.5 g, 20.8 mmol) and $K_3PO_4$ (44.2 g, 208.3 mmol). A mixture of deaerated 1,4-dioxane/water (3:1, 1 L) was added and the reaction mixture was heated to 82° C. under an argon atmosphere overnight. After cooling down to room temperature, the crude product was extracted with a DCM/aqueous $K_2CO_3$ mixture, the extract evaporated under reduced pressure and dried. Further purification was achieved via silica gel column chromatography and recrystallization from methanol/DCM (100:3, 515 mL) to yield 27.7 g (69%) of a white solid after drying.

APCI-MS: m/z=385 ([M]$^+$).

5'-(pyridin-3-yl)-[1,1': 4',1"-terphenyl]-2'-yl trifluoromethanesulfonate

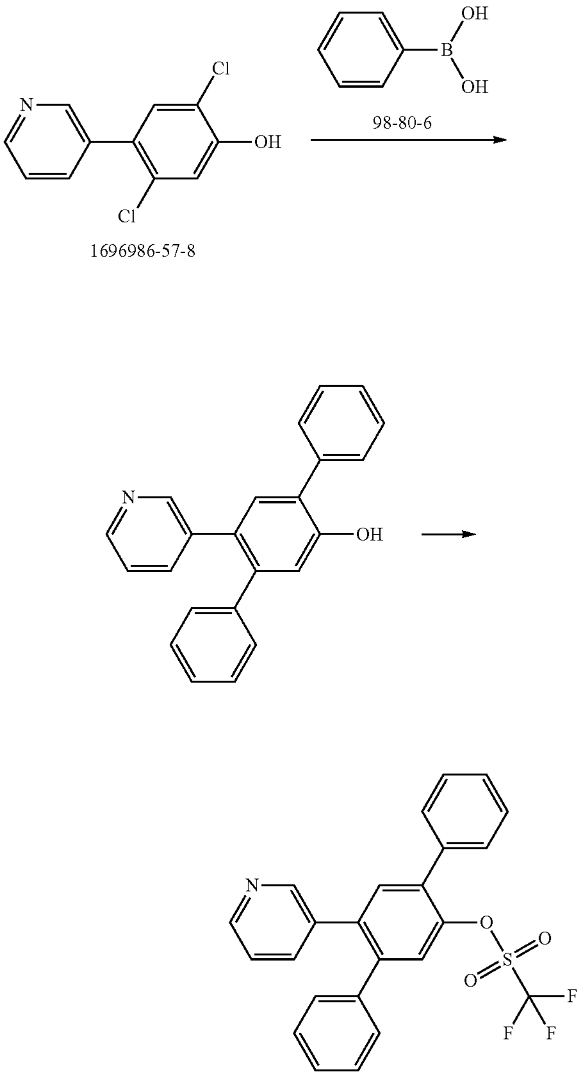

Step 1

5'-(pyridin-3-yl)-[1,1':4',1"-terphenyl]-2'-ol

A flask was flushed with argon and charged with 2,5-dichloro-4-(pyridin-3-yl)phenol (52.5 g, 218.6 mmol), phenylboronic acid (80.8 g, 218.6 mmol), $Pd(OAc)_2$ (2.9 g, 13.1 mmol), SPhos (9.0 g, 21.9 mmol) and $K_3PO_4$ (232.0 g, 1.1 mol). A mixture of deaerated toluene/water (2:1, 1.4 L) was added and the reaction mixture was heated to reflux under an argon atmosphere for 30 h. After cooling down to room temperature, the crude product was isolated by suction filtration and washed with water (0.7 L) and toluene. Further purification was achieved by acetone Soxhlet extraction to yield 55.3 g (78%) of a yellow solid after drying.

Step 2

5'-(pyridin-3-yl)-[1,1': 4',1"-terphenyl]-2'-yl trifluoromethanesulfonate

A flask was flushed with argon and charged with 5'-(pyridin-3-yl)-[1,1': 4',1"-terphenyl]-2'-ol (59.5 g, 184.0 mmol), pyridine (anhydrous, 22.2 mL, 275.9 mmol) and DCM (anhydrous, 1.2 L). The mixture was cooled to 0° C. and $Tf_2O$ (46.4 mL, 275.9 mmol) was added. After stirring under an argon atmosphere for 45 min, the reaction mixture was quenched with water (0.5 L). The crude product was extracted with a DCM/aqueous $K_2CO_3$ mixture, then the organic phase was concentrated under reduced pressure to 0.5 L, and filtered through a silica gel pad which was rinsed with DCM/EtOAc (10:1). The solvent was removed under reduced pressure, and the product was stirred overnight in petroleum ether/DCM (65:3, 680 mL) and filtered to yield 51.2 g (61%) of a white solid after drying.

APCI-MS: m/z=456 ($[M+H]^+$).

Preparation of Exemplary Compounds 2-(dibenzo[b,d]furan-3-yl)-4-phenyl-6-(5'-phenyl-4'-(pyridin-3-yl)-[1,1':2'1"-terphenyl]-4-yl)-1,3,5-triazine (E1)

A flask was flushed with nitrogen and charged with 3-(5'-bromo-[1,1': 4',1"-terphenyl]-2'-yl)pyridine (7.4 g, 19.3 mmol), 2-(dibenzo[b,d]furan-3-yl)-4-phenyl-6-(4-(4,4,5,5-tetramethyl-1,3,2-dioxaborolan-2-yl)phenyl)-1,3,5-triazine (10.0 g, 19.1 mmol), $Pd(dppf)Cl_2$ (0.3 g, 0.4 mmol), and $K_2CO_3$ (5.3 g, 38.1 mmol). A mixture of deaerated THF/water (4:1, 125 mL) was added and the reaction mixture was heated to reflux under a nitrogen atmosphere overnight. After cooling down to room temperature, the resulting precipitate was isolated by suction filtration and washed with water (until pH neutral) and methanol (2×50 mL). The crude product was then dissolved in chloroform (1.7 L) at reflux and filtered through a silica gel pad. Impurities were flushed with additional chloroform, then the product was rinsed with chloroform/methanol (98:2, 3 L). The filtrate was concentrated under reduced pressure to 200 mL and 100 mL n-hexane was added. The precipitate was collected by suction filtration to yield 11.8 g (87%) of a white solid after drying. Final purification was achieved by sublimation.

ESI-MS: m/z=705 ($[M+H]^+$).

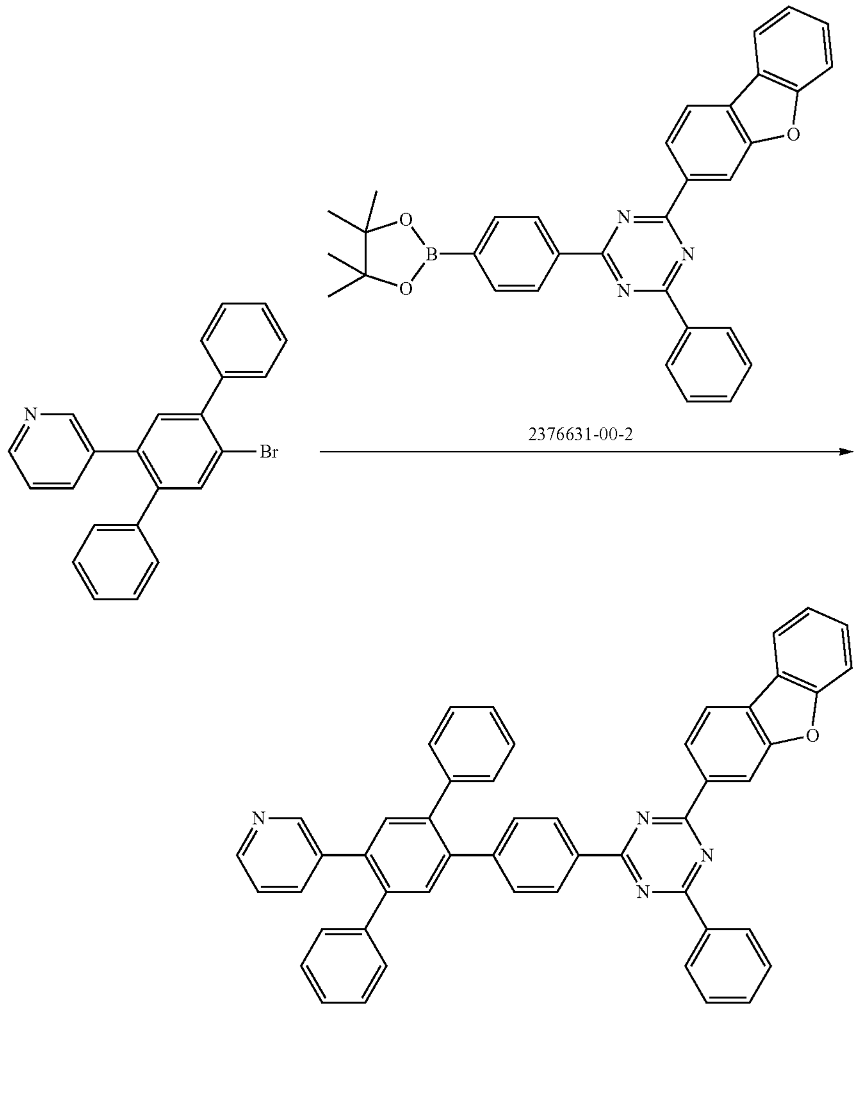

2,4-diphenyl-6-(5'-phenyl-4'-(pyridin-4-yl)-[1,1':2',1"-terphenyl]-4-yl)-1,3,5-triazine (E2)

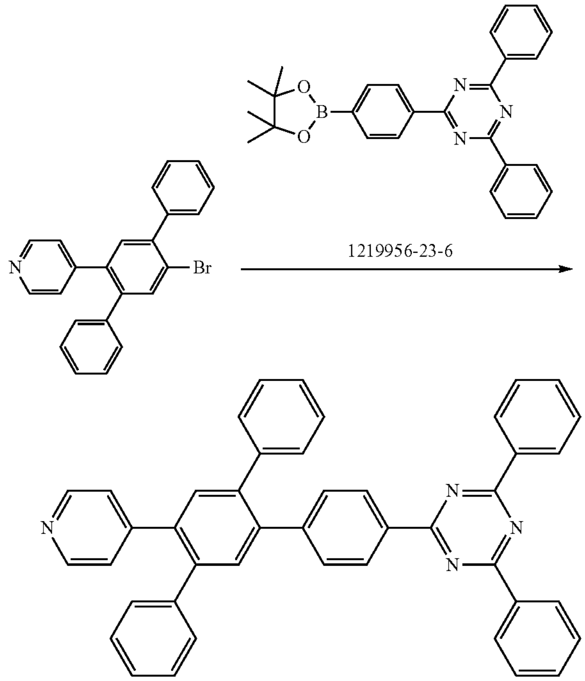

A flask was flushed with nitrogen and charged with 4-(5'-bromo-[1,1':4',1"-terphenyl]-2'-yl)pyridine (13.0 g, 33.7 mmol), 2,4-diphenyl-6-(4-(4,4,5,5-tetramethyl-1,3,2-dioxaborolan-2-yl)phenyl)-1,3,5-triazine (19.2 g, 44.0 mmol), $Pd(PPh_3)_4$ (0.8 g, 0.7 mmol), and $K_2CO_3$ (9.3 g, 67.5 mmol). A mixture of deaerated 1,4-dioxane/water (4:1, 170 mL) was added and the reaction mixture was heated to 75° C. under a nitrogen atmosphere overnight. After cooling down to room temperature, the resulting precipitate was isolated by suction filtration and washed with water (until pH neutral) and methanol (300 mL). The crude product was then dissolved in chloroform (1.5 L) at reflux and filtered through a silica gel pad. After rinsing with additional chloroform/methanol (98:2), the filtrate was concentrated under reduced pressure to 200 mL. The precipitate was collected by suction filtration, washed with n-hexane (500 mL) and further purified by recrystallization from chloroform to yield 12.0 g (58%) of a white solid after drying. Final purification was achieved by sublimation.

ESI-MS: m/z=615 ($[M+H]^+$).

2-(naphthalen-2-yl)-4-phenyl-6-(5'-phenyl-4'-(pyridin-3-yl)-[1,1': 2',1"-terphenyl]-4-yl)-1,3,5-triazine (E3)

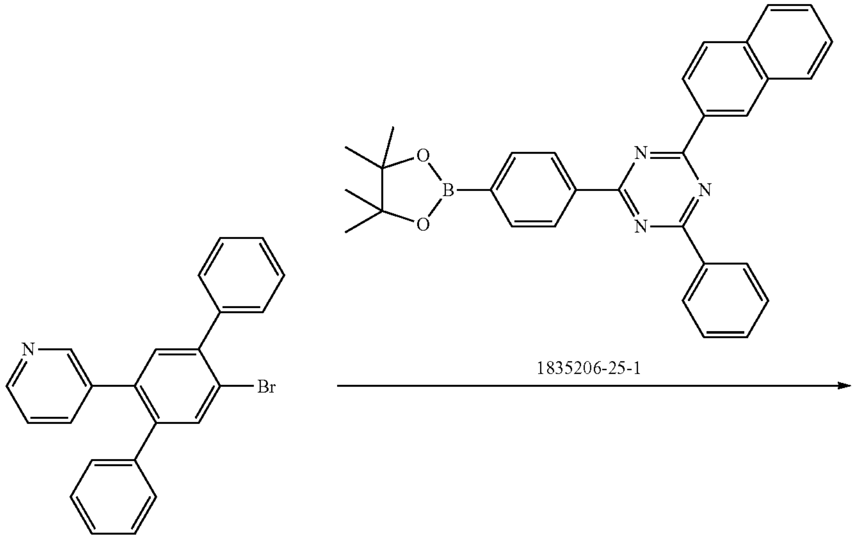

-continued

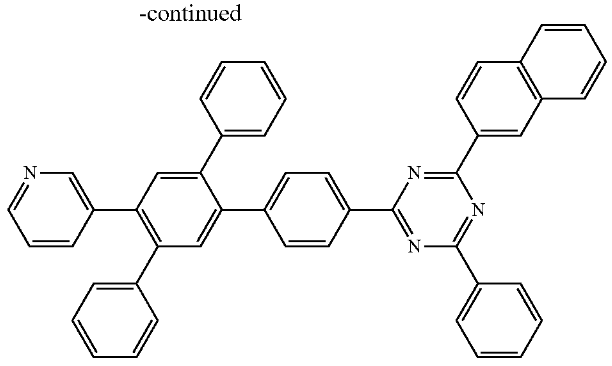

A flask was flushed with nitrogen and charged with 3-(5'-bromo-[1,1': 4',1"-terphenyl]-2'-yl)pyridine (10.0 g, 25.9 mmol), 2-(naphthalen-2-yl)-4-phenyl-6-(4-(4,4,5,5-tetramethyl-1,3,2-dioxaborolan-2-yl)phenyl)-1,3,5-triazine (12.6 g, 25.9 mmol), $Pd(dppf)Cl_2$ (0.4 g, 0.5 mmol), and $K_2CO_3$ (7.1 g, 51.7 mmol). A mixture of deaerated 1,4-dioxane/water (4:1, 125 mL) was added and the reaction mixture was heated to reflux under a nitrogen atmosphere overnight. After cooling down to room temperature, the resulting precipitate was isolated by suction filtration and washed with water (until pH neutral) and methanol (400 mL). The crude product was then dissolved in chlorobenzene (800 mL) at reflux and filtered through a silica gel pad. Impurities were flushed with additional chlorobenzene, then the product was rinsed with chloroform/methanol (98:2, 2 L) and the filtrate was concentrated under reduced pressure to 200 mL. The precipitate was collected by suction filtration, washed with n-hexane (500 mL) and further purified by recrystallization from chloroform to yield 9.0 g (52%) of a white solid after drying. Final purification was achieved by sublimation.

ESI-MS: m/z=665 ($[M+H]^+$).

2,4-diphenyl-6-(5'-phenyl-4'-(pyridin-3-yl)-[1,1':2',1"-terphenyl]-4-yl)-1,3,5-triazine (E4)

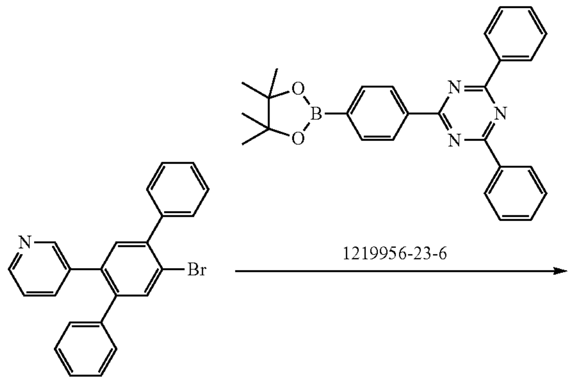

-continued

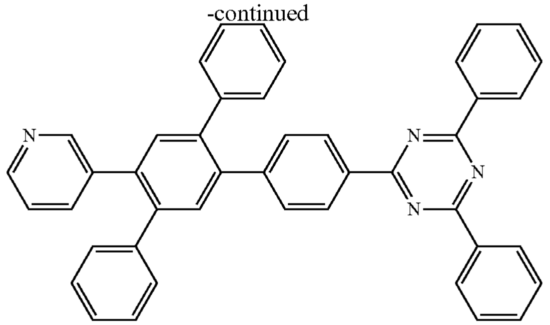

A flask was flushed with nitrogen and charged with 3-(5'-bromo-[1,1': 4',1"-terphenyl]-2'-yl)pyridine (10.0 g, 25.9 mmol), 2,4-diphenyl-6-(4-(4,4,5,5-tetramethyl-1,3,2-dioxaborolan-2-yl)phenyl)-1,3,5-triazine (12.4 g, 28.5 mmol), $Pd(dppf)Cl_2$ (0.2 g, 0.3 mmol), and $K_2CO_3$ (7.2 g, 51.8 mmol). A mixture of deaerated THF/water (4:1, 130 mL) was added and the reaction mixture was heated to reflux under a nitrogen atmosphere overnight. After cooling down to room temperature, the resulting precipitate was isolated by suction filtration and washed with water (200 ml), methanol (50 mL) and n-hexane (50 mL). The crude product was then dissolved in chlorobenzene (600 mL) at reflux and filtered through a silica gel pad. Impurities were flushed with additional hot chlorobenzene (1.5 L), then the product was rinsed with chlorobenzene/methanol (95:5, 3 L) and the filtrate was concentrated under reduced pressure. The precipitate was collected by suction filtration to yield 3.9 g (25%) of a white solid after drying.

ESI-MS: m/z=615 ([M+H]+).

Device

The inventive compounds E1 to E3 were tested as electron transport material (ETM) in a model top emitting blue OLED and compared with state-of-art compound C1 as electron transport material (ETM).

Inventive ETM Examples "E1 to E3"
E1
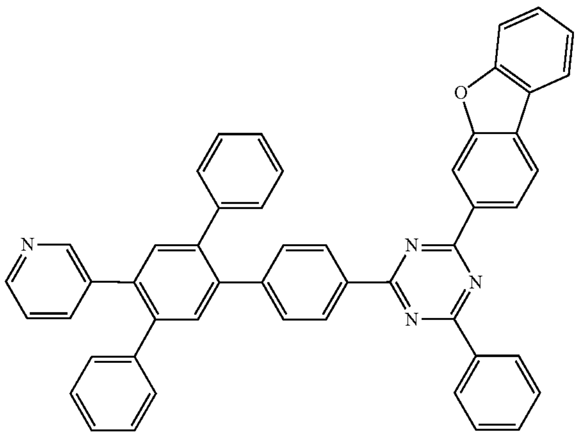
E2
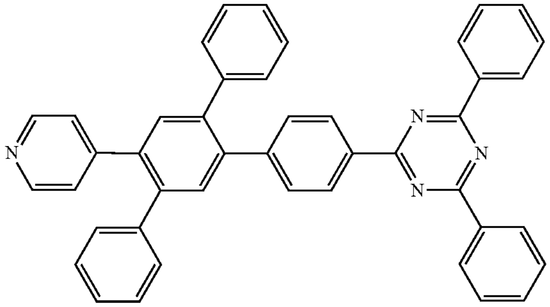
E3
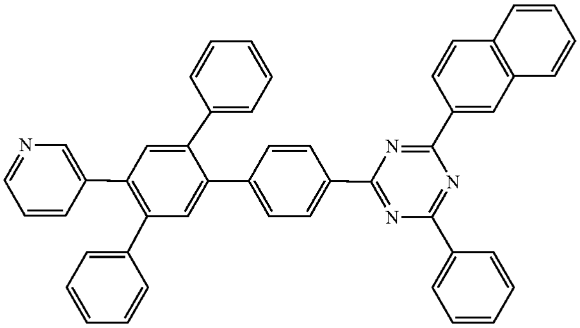
Comparative ETM Example "C1"
C1
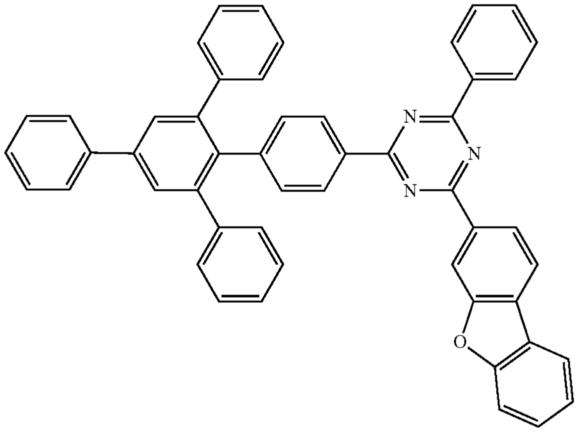
C1 (disclosed as exemplary compound D2 in WO2019/121672).
Further Supporting Materials for Preparation of a Device
F1 is
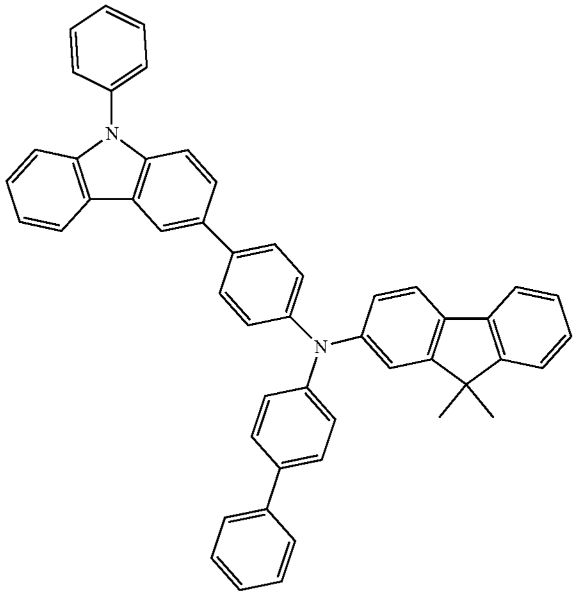 [SMILES: CC1(C)c2ccccc2-c2ccc(N(c3ccc(-c4ccccc4)cc3)c3ccc(-c4ccc5c(c4)c4ccccc4n5-c4ccccc4)cc3)cc21]
N-([1,1'-biphenyl]-4-yl)-9,9-dimethyl-N-(4-(9-phenyl-9H-carbazol-3-yl)phenyl)-9H-fluoren-2-amine, CAS 1242056-42-3;

F2 is

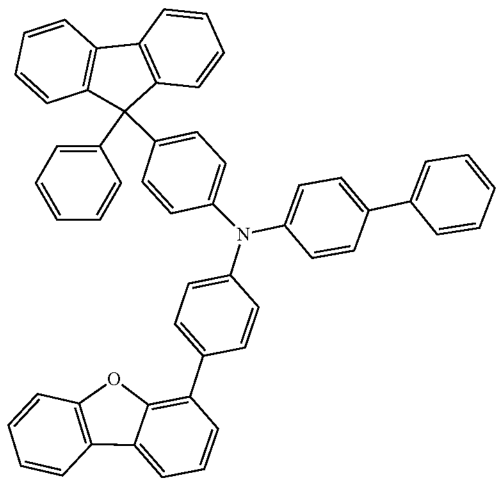 [SMILES: c1ccc(-c2ccc(N(c3ccc(-c4cccc5c4oc4ccccc45)cc3)c3ccc(C4(c5ccccc5)c5ccccc5-c5ccccc54)cc3)cc2)cc1]

N-(4-(dibenzo[b,d]furan-4-yl)phenyl)-N-(4-(9-phenyl-9H-fluoren-9-yl)phenyl)-[1,1'-biphenyl]-4-amine, CAS 1824678-59-2;

F3 is

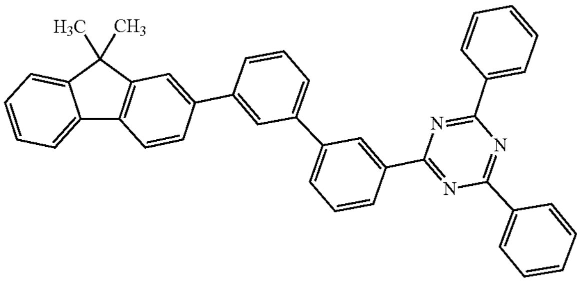 [SMILES: CC1(C)c2ccccc2-c2ccc(-c3cccc(-c4cccc(-c5nc(-c6ccccc6)nc(-c6ccccc6)n5)c4)c3)cc21]

2-(3'-(9,9-dimethyl-9H-fluoren-2-yl)-[1,1'-biphenyl]-3-yl)-4,6-diphenyl-1,3,5-triazine, CAS 1955543-57-3;

LiQ is lithium 8-hydroxyquinolinolate, H09 is a commercial blue emitter host and BD200 is a commercial blue emitter, both supplied by SFC, Korea;

PD2 is

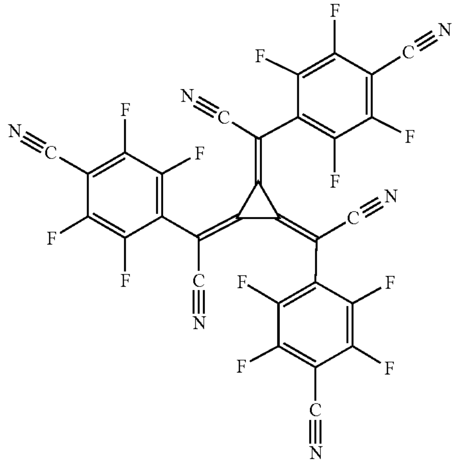 [SMILES: N#CC(=C1C(=C(C#N)c2c(F)c(F)c(C#N)c(F)c2F)C1=C(C#N)c1c(F)c(F)c(C#N)c(F)c1F)c1c(F)c(F)c(C#N)c(F)c1F]

4,4',4"-((1E,1'E,1"E)-cyclopropane-1,2,3-triylidenetris(cyanomethanylylidene))tris(2,3,5,6-tetrafluorobenzonitrile), CAS 1224447-88-4.

Standard Procedures

OLED Preparation

On a commercially available substrate provided with an anode, organic layers were deposited by vacuum thermal evaporation (VTE) in the desired order and with thicknesses/composition which can be adjusted and controlled by monitoring the deposition rate and adjusting the temperature of vaporization source for each respective component. Metallic cathodes are prepared by VTE, in case of top-emitting devices, an additional organic light outcoupling may be provided on top of the cathode. Finally, the complete OLED stack may be protected from ambient conditions by suitable encapsulation, e.g. with a glass slide, and the formed cavity may comprise a getter material for moisture and/or oxygen absorption.

To assess the performance of the inventive and comparative examples, the current efficiency is measured at 20° C. The current-voltage characteristic is determined using a Keithley 2635 source measure unit, by sourcing a voltage in V and measuring the current in mA flowing through the device under test. The voltage applied to the device is varied in steps of 0.1V in the range between 0V and 10V. Likewise, the luminance-voltage characteristics and CIE coordinates are determined by measuring the luminance in cd/m$^2$ using an Instrument Systems CAS-140CT array spectrometer (calibrated by Deutsche Akkreditierungsstelle (DAkkS)) for each of the voltage values. The cd/A efficiency at 10 mA/cm2 is determined by interpolating the luminance-voltage and current-voltage characteristics, respectively.

Lifetime LT of the device is measured at ambient conditions (20° C.) and 30 mA/cm$^2$, using a Keithley 2400 source meter, and recorded in hours.

The brightness of the device is measured using a calibrated photo diode. The lifetime LT is defined as the time till the brightness of the device is reduced to 97% of its initial value.

Voltage Stability

OLEDs are driven by constant current circuits. Those circuits can supply a constant current over a given voltage range. The wider the voltage range, the wider the power losses of such devices. Hence, the change of driving voltage upon driving needs to be minimized.

The driving voltage of an OLED is temperature dependent. Therefore, voltage stability needs to be judged in thermal equilibrium. Thermal equilibrium is reached after one hour of driving.

Voltage stability is measured by taking the difference of the driving voltage after 50 hours and after 1 hour driving at a constant current density. Here, a current density of 30 mA/cm$^2$ is used. Measurements are done at room temperature.

$$dU\ [\mathrm{V}] = U(50\ \mathrm{h}, 30\ \mathrm{mA/cm^2}) - U(1\ \mathrm{h}, 30\ \mathrm{mA/cm^2})$$

Device Structure

The model device for testing the inventive compounds was a blue top emitting OLED with a structure schematically shown in Table 1.

TABLE 1

| Layer | Material | d [nm] |
|---|---|---|
| Anode | Ag | 100 |
| HIL | F1:PD2 (92:8 v/v) | 10 |

TABLE 1-continued

| Layer | Material | d [nm] |
|---|---|---|
| HTL | F1 | 128 |
| EBL | F2 | 5 |
| EML | H09:BD200 (97:3 v/v) | 20 |
| HBL | F3 | 5 |
| ETL | ETM:LiQ (50:50 v/v) | 31 |
| EIL | Yb | 2 |
| Cathode | Ag:Mg (90:10) | 11 |

Test Results

Test result with respect to the lifetime (LT) and the voltage stability (dV) observed for the model device in case that E1, E2, E3 and C1 were used as ETM, respectively, are shown in Table 2

TABLE 2

| ETM | LT (h) | dV (V) |
|---|---|---|
| C1 | 56 | 0.033 |
| E1 | 80 | 0.006 |
| E2 | 72 | 0.004 |
| E3 | 74 | 0.005 |

As it can be seen from Table 2, if the inventive compounds E1 to E3 were used as ETM, both lifetime as well as voltage stability of the tested device was significantly improved in comparison to the comparative compound C1.

The invention claimed is:

1. Compound of the following Formula (I)

(I)

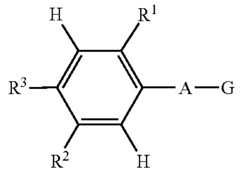

wherein

A is substituted or unsubstituted phenylene, wherein, in case that A is substituted, the one or more substituent (s) are independently selected hydrocarbyl groups;

G is (i) substituted or unsubstituted $C_{10}$ to $C_{60}$ aryl comprising at least two condensed aromatic rings; or (ii) substituted or unsubstituted $C_3$ to $C_{60}$ heteroaryl comprising at least one six-membered ring, wherein the six-membered ring comprises at least two N-atoms; or (iii) substituted or unsubstituted heteroaryl comprising at least two condensed aromatic rings, wherein at least one of the aromatic rings is an azine ring; or (iv) selected from benzofurane, benzothiophene, dibenzothiophene, naphtofurane, naphtothiophene, naphtobenzofurane, naphtobenzothiophene, dinaphtofurane, dinaphtothiophene, xanthene, thioxanthene, dibenzodioxine, phenoxazine, phenothiazine, benzimidazole, benzoxazole, and benzothiazole, wherein the respective group may be unsubstituted or substituted; or (v) selected from fluorene, benzofluorene, dibenzofluorene, naphtofluorene, dinaphtofluorene, benzonaphtofluorene, 9-silafluorene, benzo 9-silafluorene, dibenzo 9-silafluorene, naphto 9-silafluorene, dinaphto 9-silafluorene, and benzonaphto 9-silafluorene;

$R^1$ is (i) H; or (ii) substituted or unsubstituted pyridyl, wherein, in case that $R^1$ is substituted, the one or more substituent(s) are independently selected from the group consisting of $C_1$ to $C_{20}$ aliphatic hydrocarbyl and nitrile; or (iii) substituted or unsubstituted phenyl, wherein, in case that $R^1$ is substituted, the one or more substituent(s) are nitrile; or (iv) a phosphine oxide group;

$R^2$ and $R^3$ are independently (i) substituted or unsubstituted pyridyl, wherein, in case that $R^2$ and/or $R^3$ are substituted, the one or more substituent(s) are independently selected from the group consisting of $C_1$ to $C_{20}$ aliphatic hydrocarbyl and nitrile; or (ii) substituted or unsubstituted phenyl wherein, in case that $R^2$ and/or $R^3$ are substituted, the one or more substituent(s) are independently selected from the group consisting of $C_1$ to $C_{20}$ aliphatic hydrocarbyl and nitrile; or (iii) a phosphine oxide group;

with the proviso that at least one of $R^1$, $R^2$ and $R^3$ is (i) substituted or unsubstituted pyridyl, wherein the one or more substituent(s) on the pyridyl, if present, are independently selected from the group consisting of $C_1$ to $C_{20}$ aliphatic hydrocarbyl and nitrile; or (ii) substituted phenyl wherein (a) the one or more substituent(s) of the phenyl are independently selected from the group consisting of C to $C_{20}$ aliphatic hydrocarbyl and nitrile, and (b) at least one of the substituents is nitrile; or (iii) a phosphine oxide group.

2. Compound according to claim 1, wherein A is unsubstituted phenylene.

3. Compound according to claim 1, wherein G is (i) substituted or unsubstituted $C_{10}$ to $C_{60}$ aryl comprising at least two condensed aromatic rings; or (ii) substituted or unsubstituted $C_3$ to $C_{60}$ heteroaryl comprising at least one six-membered ring, wherein the six-membered ring comprises at least two N-atoms; or (iii) substituted or unsubstituted heteroaryl comprising at least two condensed aromatic rings, wherein at least one of the aromatic rings is an azine ring.

4. Compound according to claim 1, wherein G is represented by the following Formula (II)

(II)

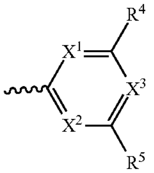

wherein

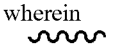 represents the binding to the group A;

$X^1$ to $X^3$ are independently selected from the group consisting of N and CH, wherein at least two of $X^1$ to $X^3$ are N; and $R^4$ and $R^5$ are independently selected from the group consisting of $C_6$ to $C_{30}$ aryl and $C_3$ to $C_{30}$ heteroaryl.

5. Compound according to claim 1, wherein $R^1$ is H, phenyl, pyridyl or phenyl substituted with one nitrile.

6. Compound according to claim 1, wherein $R^2$ and $R^3$ are independently selected from the group consisting of phenyl, pyridyl and phenyl substituted with one nitrile.

7. Compound according to claim 1, wherein at least one of $R^2$ and $R^3$ is selected from unsubstituted pyridyl, pyridyl substituted with at least one $C_1$ to $C_{20}$ aliphatic hydrocarbyl, and phenyl substituted with at least one nitrile group.

8. Compound according to claim 1, wherein $R^1$ is H or phenyl and at least one of $R^2$ and $R^3$ is selected from unsubstituted pyridyl, pyridyl substituted with at least one $C_1$ to $C_{20}$ aliphatic hydrocarbyl, and phenyl substituted with at least one nitrile group.

9. Organic semiconducting material comprising the compound of Formula (I) according to claim 1.

10. Organic electronic device comprising a first electrode, a second electrode and an organic semiconducting layer arranged between the first electrode and the second electrode, wherein the semiconducting layer comprises a compound of Formula (I) according to claim 1.

11. Organic electronic device according to claim 10, wherein the semiconducting layer comprising the compound of Formula (I) is an electron transport layer, an electron injection layer, a hole blocking layer or an electron generating layer.

12. Display device comprising an organic electronic device according to claim 10.

13. A method of manufacturing an organic electronic device, the method comprising forming an organic semiconducting layer comprising a compound of Formula (I) according to claim 1.

14. Process for preparing a compound of Formula (I) according to claim 1

(I)

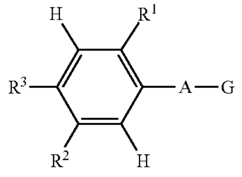

the process comprising reacting a compound of the following formula (IV) and a compound of the following formula (V)

(IV)

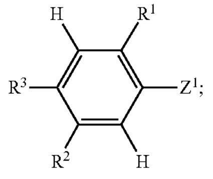

(V)

$$Z^2—A—G,$$

wherein

A is substituted or unsubstituted phenylene, wherein, in case that A is substituted, the one or more substituent (s) are independently selected hydrocarbyl groups;

G is (i) substituted or unsubstituted $C_{10}$ to $C_{60}$ aryl comprising at least two condensed aromatic rings; or (ii) substituted or unsubstituted $C_3$ to $C_{60}$ heteroaryl comprising at least one six-membered ring, wherein the six-membered ring comprises at least two N-atoms; or (iii) substituted or unsubstituted heteroaryl comprising at least two condensed aromatic rings, wherein at least one of the aromatic rings is an azine ring; or (iv) selected from benzofurane, benzothiophene, dibenzothiophene, naphtofurane, naphtothiophene, naphtobenzofurane, naphtobenzothiophene, dinaphtofurane, dinaphtothiophene, xanthene, thioxanthene, dibenzodioxine, phenoxazine, phenothiazine, benzimidazole, benzoxazole, and benzothiazole, wherein the respective group may be unsubstituted or substituted; or (v) selected from fluorene, benzofluorene, dibenzofluorene, naphtofluorene, dinaphtofluorene, benzonaphtofluorene, 9-silafluorene, benzo 9-silafluorene, dibenzo 9-silafluorene, naphto 9-silafluorene, dinaphto 9-silafluorene, and benzonaphto 9-silafluorene;

$R^1$ is (i) H; or (ii) substituted or unsubstituted pyridyl, wherein, in case that $R^1$ is substituted, the one or more substituent(s) are independently selected from the group consisting of $C_1$ to $C_{20}$ aliphatic hydrocarbyl and nitrile; or (iii) substituted or unsubstituted phenyl, wherein, in case that $R^1$ is substituted, the one or more substituent(s) are nitrile; or (iv) a phosphine oxide group;

$R^2$ and $R^3$ are independently (i) substituted or unsubstituted pyridyl, wherein, in case that $R^2$ and/or $R^3$ are substituted, the one or more substituent(s) are independently selected from the group consisting of $C_1$ to $C_{20}$ aliphatic hydrocarbyl and nitrile; or (ii) substituted or unsubstituted phenyl wherein, in case that $R^2$ and/or $R^3$ are substituted, the one or more substituent(s) are independently selected from the group consisting of $C_1$ to $C_{20}$ aliphatic hydrocarbyl and nitrile; or (iii) a phosphine oxide group; and $Z^1$, $Z^2$ are independently selected from the group consisting of halogen, boronic acid, sulfonic acid ester and boronate ester;

with the proviso that at least one of $R^1$, $R^2$ and $R^3$ is (i) substituted or unsubstituted pyridyl, wherein the one or more substituent(s) of the pyridyl, if present, are independently selected from the group consisting of $C_1$ to $C_{20}$ aliphatic hydrocarbyl and nitrile; or (ii) substituted phenyl wherein (a) the one or more substituent(s) of the phenyl are independently selected from the group consisting of $C_1$ to $C_{20}$ aliphatic hydrocarbyl and nitrile, and (b) at least one of the substituents is nitrile; or (iii) a phosphine oxide group.

15. Compound of the following formula (IV)

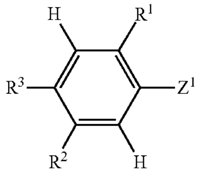

(IV)

wherein $R^1$ is (i) H; or (ii) substituted or unsubstituted pyridyl, wherein, in case that $R^1$ is substituted, the one or more substituent(s) are independently selected from the group consisting of $C_1$ to $C_{20}$ aliphatic hydrocarbyl and nitrile; or (iii) substituted or unsubstituted phenyl, wherein, in case that $R^1$ is substituted, the one or more substituent(s) are nitrile; or (iv) a phosphine oxide group;

$R^2$ and $R^3$ are independently (i) substituted or unsubstituted pyridyl, wherein, in case that $R^2$ and/or $R^3$ are substituted, the one or more substituent(s) are independently selected from the group consisting of $C_1$ to $C_{20}$ aliphatic hydrocarbyl and nitrile; or (ii) substituted or unsubstituted phenyl wherein, in case that $R^2$ and/or $R^3$ are substituted, the one or more substituent(s) are independently selected from the group consisting of $C_1$ to $C_{20}$ aliphatic hydrocarbyl and nitrile; or (iii) a phosphine oxide group and $Z^1$, $Z^2$ are groups independently selected from halogen, boronic acid group, sulfonic acid ester group and boronate ester group;

with the proviso that at least one of $R^1$, $R^2$ and $R^3$ is (i) substituted or unsubstituted pyridyl, wherein the one or more substituent(s) of the pyridyl, if present, are independently selected from the group consisting of $C_1$ to $C_{20}$ aliphatic hydrocarbyl and nitrile; or (ii) a phosphine oxide group.

* * * * *